(12) United States Patent
Dye

(10) Patent No.: US 8,273,372 B2
(45) Date of Patent: Sep. 25, 2012

(54) EXTRACELLULAR MATRIX COMPOSITION

(75) Inventor: Julian Dye, Middlesex (GB)

(73) Assignee: Restoration of Appearance & Function Trust, Northwood, Middlesex (GB)

( * ) Notice: Subject to any disclaimer, the term of this patent is extended or adjusted under 35 U.S.C. 154(b) by 752 days.

(21) Appl. No.: 12/304,907

(22) PCT Filed: Jun. 15, 2007

(86) PCT No.: PCT/GB2007/002238
§ 371 (c)(1),
(2), (4) Date: Feb. 10, 2009

(87) PCT Pub. No.: WO2007/144644
PCT Pub. Date: Dec. 21, 2007

(65) Prior Publication Data
US 2009/0324719 A1    Dec. 31, 2009

Related U.S. Application Data

(60) Provisional application No. 60/804,996, filed on Jun. 16, 2006.

(30) Foreign Application Priority Data

Jun. 16, 2006  (GB) .................................. 0611986.1
May 11, 2007  (GB) .................................. 0709099.6

(51) Int. Cl.
A61K 9/14      (2006.01)
A61K 38/36    (2006.01)
A61P 17/02    (2006.01)
(52) U.S. Cl. ......................................... 424/484; 514/12
(58) Field of Classification Search .................. 424/484; 514/12
See application file for complete search history.

(56) References Cited

U.S. PATENT DOCUMENTS 4,442,655 A    4/1984  Stroetmann
2002/0131933 A1    9/2002  Delmotte

FOREIGN PATENT DOCUMENTS

WO    WO 2004/067704 A2    8/2004

OTHER PUBLICATIONS

International Search Report, PCT/GB2007/002238, Dec. 11, 2008.
International Preliminary Report on Patentability, PCT/GB2007/002238, Jan. 20, 2009.
Examination Report from European Patent Office, Application No. 07 733 242.7, Jun. 2, 2009.

*Primary Examiner* — Chih-Min Kam
(74) *Attorney, Agent, or Firm* — Duane Morris LLP

(57) ABSTRACT

The invention relates to a process for preparing an extracellular matrix composition comprising cross-linked fibrinogen or a derivative thereof, to an extracellular matrix composition obtained by the process and to the use of the composition in wound healing, tissue regeneration or as a tissue engineering scaffold.

21 Claims, 30 Drawing Sheets

EXTRACELLULAR MATRIX COMPOSITION

Figure 1:
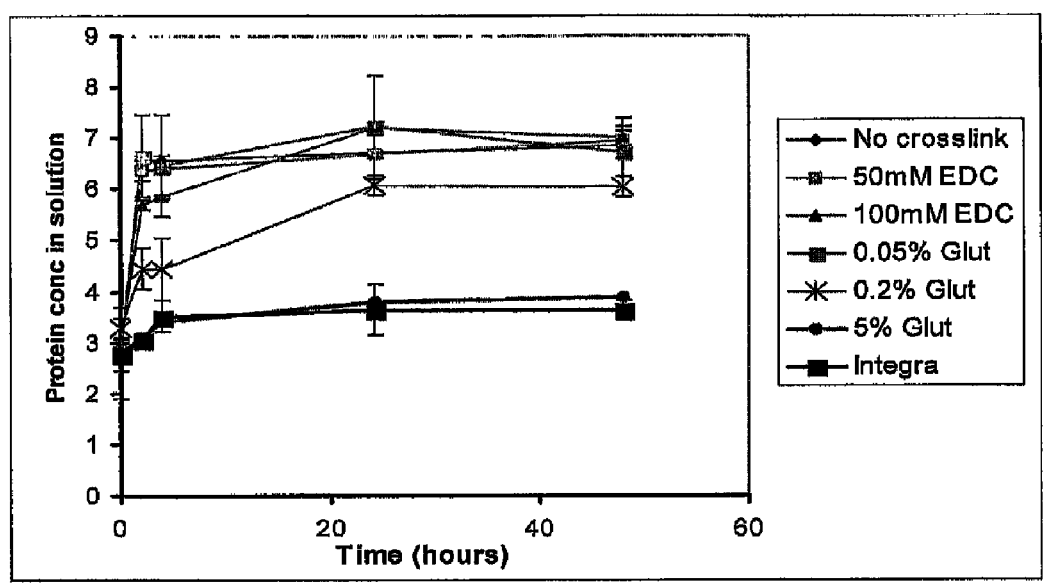

This application is a 371 of PCT/GB2007/002238, filed Jun. 15, 2007, which claims benefit of United Kingdom 0611986.1, filed Jun. 16, 2006; U.S. Provisional application. 60/804,996, filed Jun. 16, 2006; and United Kingdom 0709099.6, filed May 11, 2007.

The invention relates to a process for preparing an extracellular matrix composition comprising cross-linked fibrinogen or a derivative thereof, to an extracellular matrix composition obtained by said process and to the use of said composition in healing of full thickness skin loss wounds, tissue regeneration or as a tissue engineering scaffold.

Wounds involving full thickness skin loss encompass a broad spectrum of disease aetiology from the three principal chronic wounds: pressure ulcers, venous ulcers and diabetic ulcers to traumatic wounds and burns. Acute and chronic wounds involving full thickness skin loss are life-threatening and can be fatal. These wounds cause physiological stress, invariably expose significant structures, and are costly to treat. They can have serious consequences as they disrupt the protective function of the skin, increasing the chances of infection and leading to fluid loss. Furthermore, they can also cause the patient considerable physical, emotional, and social distress as they do not readily heal.

As scientists' basic understanding of wounds and wound healing mechanisms has progressed, a number of different approaches to the treatment of wounds have been developed. However, whilst small wounds have benefited from advances such as microsurgical flap closure and the advent of topical negative pressure, attempts at improving management techniques for large wounds have been less successful.

This is because large wounds necessitate skin cover to which there are a number of unsatisfactory solutions. Split thickness skin grafts, which remove the required tissue from the patient causing further injury, do not stimulate regeneration of lost dermis and thereby often result in severe scarring. Furthermore, cultured keratinocytes can take around a month to prepare and when applied to a wound without an adequate dermis, also result in serious long-term scarring.

For this reason, extracellular matrix compositions such as dermal scaffold compositions have been introduced into the clinical forum and are seeing increasing usage (at least in the UK) over the past decade. It has been recognised that these compositions must have particular properties to enable them to reduce wound contraction and scarring. The material must be able to support cellular adhesion; be rigid enough to resist collapse under the tractional forces exerted by in-growing cells; as well as being resistant to rapid proteolytic degradation so as to survive in a wound environment for fibroproliferation to occur.

Currently, collagen is the principal component of dermal scaffold compositions. Collagen has been regarded as a passive, permissive support to allow cell conductance. The ingress of cultured fibroblasts and endothelial cells into collagenous materials is limited. Clinical experience indicates that in difficult wounds the 'take', (i.e. the successful union of a graft with a patient's skin) of such collagen-based solutions can be several weeks. As such, they are often dogged by infection, seromas and haematomas, and they frequently fail with serious consequences.

Recent evidence suggests that fibrinogen may have critical properties relevant to angiogenesis (Potter et al. (2006) Plast. Reconstr. Surg. 117(6), 1876-1885) which is a physiological process involving the growth of new blood vessels from pre-existing vessels. Angiogenesis is particularly critical to the wound repair process with some cells unable to survive if they are >100 μm from the nearest functional capillary (Langer et al. Tissue Eng 1995:1:151-161). US 2004/0229333 (Bowlin et al) discloses a series of electroprocessed fibrin-based matrices and tissues.

Fibrinogen has been identified as a potential component in a synthetic dermis (Baldwin et al.: Development of a pro-angiogenic matrix for synthetic dermis using cultured endothelial cells. Institute Pasteur Euroconferences 40, 2005).

The object of this invention is to provide a stable, extracellular matrix composition that actively interacts with cells, particularly to promote endothelial cell adhesion, increasing the likelihood of 'take' and therefore the success of the artificial matrix material.

Thus, according to a first aspect of the invention there is provided a process for preparing an extracellular matrix composition which comprises:
(a) mixing an aqueous solution of fibrinogen with a coagulating agent and a bulking agent;
(b) incubating the mixture obtained in step (a) with a cross-linking agent; and
(c) washing the cross-linked composition obtained in step (b) to remove the cross-linking agent.

As used herein, the term "extracellular matrix" refers to a structure, scaffold or platform made up of a chemically or biochemically defined material to which various cells (e.g. dermal, muscle, nerve, connective tissue, fasca, dura or peritoneum) of higher vertebrates can adhere to and multiply without causing toxicity or inhibition of cell replication.

Fibrinogen has a molecular mass of 340 kDa (Doolittle, R. F. Annu Rev Biochem. 1984; 53:195-229) and is made up of three pairs of polypeptide chains $(A\alpha B\beta\gamma)_2$. The amino-terminal ends of all three pairs of chains are joined together by disulfide bonds in the central region of the molecule. The carboxyl-terminal ends of the Bβ chains contain the proximal end regions, and the carboxyl-terminal ends of the γ chain contain the distal end regions (Weisel, J. W., Stauffacher, C. V., Bullitt, E., Cohen, C. Science. 1985; 230:1388-1391).

Fibrinogen can be cleaved at various different sites to produce fibrin fragments. For example, fibrinogen can be split into Fragment A, B, C, and X using plasmin. Fragment X can then be split into Fragment Y and Fragment D. Fragment Y can be further split to yield another fragment D and fragment E

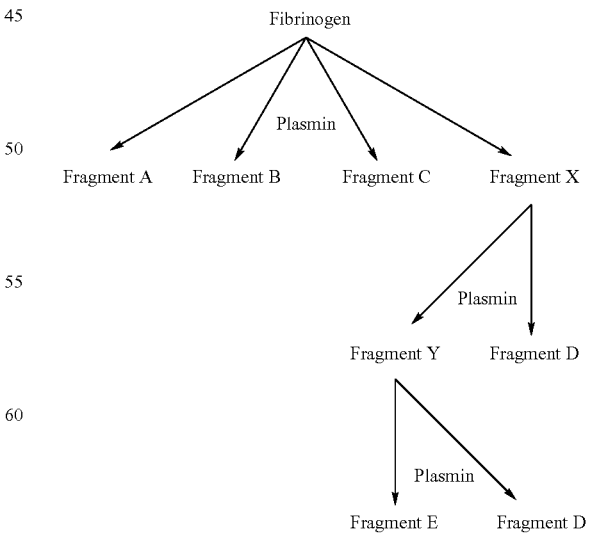

References to "fibrinogen or a derivative thereof" therefore include references to native fibrinogen purified from plasma, fragments of fibrinogen or analogues of fibrinogen. It will be appreciated that any fragment or analogue thereof should retain the angiogenic function of native fibrinogen and we have shown herein that the above mentioned degradation products mimic native fibrinogen's pro-angiogenic effect.

It will be appreciated that references to purified fibrinogen include fibrinogen at a purity level of greater than one of 75%, 80%, 85%, 90%, 95%, 97% or 99%.

Examples of fragments of fibrinogen include truncated forms of fibrinogen, such as fibrin A, fibrin B, fibrin C, fibrin D, fibrin X and fibrin Y. In a further embodiment, the truncated form of fibrinogen is fibrin E.

Examples of analogues of fibrinogen include a modified derivative of fibrinogen wherein one or more amino acid residues of the peptide have been substituted by other naturally occurring or synthetic amino acid residues and/or wherein one or more amino acid residues have been deleted from the peptide and/or wherein one or more amino acid residues have been added to the peptide. Such addition or deletion of amino acid residues can take place at the N-terminal of the peptide and/or at the C-terminal of the peptide. A further example may be a genetically recombinant fibrinogen molecule.

It will be appreciated that references to fibrinogen or a derivative do not extend to electroprocessed fibrinogen or a derivative thereof such as those described in US 2004/0229333.

The presence of fibrinogen or a derivative thereof in the composition has an intrinsic and potent stimulatory effect on endothelial cell migration, which leads to improved take and allows a significantly more rapid healing process. It is therefore believed that the porous fibrin matrix obtained by the process of the invention may represent a more effective treatment of wounds than previously described extracellular matrix compositions (e.g. dermal skin scaffolds).

In one embodiment, fibrinogen is present within the composition as an aqueous solution buffered to a pH of between 4 and 10. In a further embodiment, fibrinogen is buffered to a pH of between 7 and 8 (e.g. 7.4). In one embodiment, fibrinogen is buffered with phosphate buffered saline (PBS) or HEPES buffered saline.

In one embodiment, the coagulating agent comprises an enzymatic or non-enzymatic coagulating agent. In a further embodiment, the enzymatic coagulating agent is thrombin (IUBMB Enzyme nomenclature EC3.4.21.5) or a thrombin mimetic. The presence of thrombin or a thrombin mimetic within the extracellular matrix assists with formation of a stable composition in the form of a gel.

In one embodiment, the enzymatic coagulating agent is thrombin which may be derived from the animal or prokaryotic kingdom. In a further embodiment, the enzymatic-coagulating agent is salmon thrombin. This embodiment provides the advantage of reducing the risk for transmission of infectious disease. In an alternative embodiment, the enzymatic-coagulating agent is human thrombin.

Thrombin is a chymotrypsin family endopeptidase, with trypsin-like substrate specificity. Thrombin converts fibrinogen into fibrin by selectively cleaving Arg-Gly bonds in fibrinogen to release fibrinopeptides A and B.

Thrombin is also described as a fibrinogenase, thrombase, thrombofort, topical thrombin-C, tropostasin, activated blood-coagulation factor II, blood-coagulation factor IIa, factor IIa, E thrombin, β-thrombin, and γ-thrombin. Therefore, references to a thrombin mimetic includes any structurally and functionally related agents, analogues and all derivatives thereof which demonstrate these properties. Examples of such thrombin mimetics include: Batroxobin (synonyms: defibrase, reptilase; IUBMB nomenclature S01.176); Crotalase (derived from Crotalus adamanteus venom; synonyms: defibrinzyme; IUBMB nomenclature S01.177); Bothrombin (derived from Bothrops jararaca venom; IUBMB nomenclature S01.179); Atroxin (derived from Bothrops atrox; IUBMB nomenclature U9G.05); Ancrod (derived from Agkistrodon controtix toxin; synonyms Arvin, Protac, Protein C activator; IUBMB nomenclature S01.178); and Gabonase (derived from Bitis gabonica; IUBMB nomenclature S01.430).

In one embodiment, the non-enzymatic coagulating agent is protamine or hyaluronan.

In one embodiment, step (a) of the process additionally comprises mixing an aqueous solution of fibrinogen with a foaming agent. Examples of a foaming agent include a surfactant, a block co-polymer surfactant such as a pluronic surfactant, detergent or the like. The presence of a foaming agent provides the benefit of creating an effective foam structure while being capable of being easily removed from the composition, for example, by dissolving in ethanol in the case of a surfactant or by reduction of the calcium ion concentration to dissolve out a calcium dependent bead gel in the case of a micro-bead. In a further embodiment, the foaming agent comprises a surfactant, such as a non-ionic detergent, thermosensitive gelling surfactant (e.g. pluronic 127), diphosphatydylglycerol type phospholipid or a mixture of an immiscible phase (e.g. isopentane) with the aqueous fibrinogen solution phase.

The presence of a bulking agent within step (a) provides the advantage of initiating formation of the extracellular matrix and synergistically controls the microstructure of the resultant mixture.

Examples of bulking agents include: alginates; biopolymers including xanthan gum and scleroglucan; carboxymethylcellulose; carrageenans (e.g. galactose sulfate); galactomannans i.e. locust bean gum and guar gum flower; hetastarch; a differentially soluble inert micro-bead; glycosaminoglycans (GAG; e.g. chondroitin 6-sulfate, chondroitin 4-sulfate, heparin, heparin bulphate, keratan sulfate, dermatan sulfate, chitin, chitosan, dextran sulphate or hyaluronan) and locust bean gum refined extracts, such as lecithins and pectins.

In one embodiment, the bulking agent is an alginate or derivatized alginate. In a further embodiment, the bulking agent is sodium alginate or sodium propylglycoalginate. The presence of alginate within the extracellular matrix composition induces a calcium-independent co-precipitation reaction which provides the advantage of assisting with formation of a stable composition in the form of a gel.

Alginates are salts of alginic acid, which is a polyuronide made up of a sequence of two hexuronic acid residues: β-D-mannuronic acid (or M-residue); and α-L-guluronic acid (or G-residue). α-L-Guluronic acid is formed from enzymic epimerisation of β-D-mannuronic acid. These monomers can appear in homopolymeric blocks of consecutive G-residues (G-blocks), consecutive M-residues (M-blocks), alternating M and G-residues (MG-blocks) or randomly organized blocks. The relative amount of each block type varies both with the origin of the alginate. Alternating blocks form the most flexible chains and are more soluble at lower pH than the other blocks. G-blocks are more suitable as they form stronger gels than M-rich chains on the addition of divalent cations, e.g. $Ca^{2+}$, $Ba^{2+}$, $Sr^{2+}$, $Cu^{2+}$ etc. This is because two G-blocks of more than 6 residues can form stable cross-linked junctions with divalent cations leading to a three-dimensional gel network (Simpson-N E, et al., Biomaterials 25 (2004) 2603-2610).

In an alternative embodiment, the bulking agent is a glycosaminoglycan (GAG; e.g. chondroitin 6-sulfate, chondroitin 4-sulfate, heparin, heparin sulphate, keratan sulfate, dermatan sulfate, chitin, chitosan, dextran sulphate or hyaluronan). The presence of a GAG within the composition provides the advantage of stability enhancement by virtue of possessing amino acid residues which may be covalently cross-linked to fibrinogen during cross-linking of fibrinogen.

It will be appreciated that a variety of methods can be used to form the fibrinogen-based mixture prepared in process (a) any of which will result in porous matrices to form tissue scaffolds. Thus, in one embodiment, step (a) may alternatively or additionally comprise a casting, phase separation casting, foaming, lyophilising, extrusion, textiling, felting, spray coating or rapid manufacture step.

The cross-linking agent used in step (b) may be any one of a number of cross-linking agents or cross-linking techniques commonly known to those skilled in the art, such as chemical, radiation and dehydrothermal methods. An additional advantage provided by extracellular matrix compositions comprising cross-linked fibrinogen is removal of bacteria growths from the materials. Thus, the compositions of the invention are simultaneously sterilised during cross-linking. In addition, we have shown that the presence of cross-linking allows the composition's physical and therapeutic properties to create a synergy, which provides significant advantages when compared with non-cross-linked fibrinogen or a derivative thereof or other dermal skin scaffolds.

Examples of suitable chemical cross-linking agents include: carbodiimide coupling agents such as N-(3-dimethylaminopropyl)-N'-ethylcarbodiimide (EDC); N-hydroxysuccinimide (NHS), azide coupling agents; diisocyanate cross-linking agents such as hexamethylene diisocyanate; epoxide cross-linking agents such as epi-chlorhydrin, glycidylethers and glycidylamines; and aldehyde cross-linking agents such as formaldehyde, glutaraldehyde and glyoxal.

In a further embodiment the chemical cross linking agent comprises N-(3-dimethylaminopropyl)-N'-ethylcarbodiimide (EDC) and/or N-hydroxysuccinimide (NHS).

In an alternative embodiment the chemical cross linking agent comprises aldehyde cross-linking agents such as formaldehyde, glutaraldehyde and glyoxal. Aldehyde cross-linking agents have the advantage of providing extracellular matrix compositions with improved biocompatibility. For example, we have shown herein that the presence of an aldehyde crosslinking agent enhances in vitro spreading (e.g. seeding of human endothelial cells or fibroblasts onto the matrix). In a further embodiment, the aldehyde cross-linking agent is glutaraldehyde. The use of glutaraldehyde as a cross-linking agent provides a surprising advantage of yielding an optimal cross-link density more rapidly than other aldehydes and is also capable of achieving a relatively high density of cross-linking.

When the cross-linking agent comprises glutaraldehyde or N-(3-dimethylaminopropyl)-N'-ethylcarbodiimide (EDC) and/or N-hydroxysuccinimide (NHS), step (b) may additionally comprise the addition of a toxicity reducing agent (e.g. lysine).

In one embodiment, when the bulking agent comprises alginate, the process of the invention may comprise an additional cross-linking step to cross link alginate to fibrinogen. In a further embodiment, the cross-linking agent comprises periodic acid. Such an additional cross-linking step is likely to enhance the stability of the resultant composition.

The incubation step (b) may typically be performed from between 1 minute and 24 hours (e.g. 4 hours) at a suitable temperature (e.g. room temperature).

When the cross-linking agent comprises an aldehyde cross-linking agent, the process may additionally comprise the addition of a reducing agent following step (b) and prior to step (c).

The presence of the reducing agent is believed to stabilise the cross-linking process and surprisingly results in an extracellular matrix composition with enhanced biological efficacy. Furthermore, the presence of the reducing agent is likely to reduce the cytotoxic effects caused by the leaching of un-reduced cross-linking agent from the composition.

Examples of a suitable reducing agent include sodium borohydride or agents with similar carbonyl group reactivity.

The reducing agent may typically be added in an amount of between 0.1% w/w and 10% w/w (e.g. 1% w/w).

Glutaraldehyde exists in a number of differing conformations. For example, at acidic pH, glutaraldehyde is in equilibrium with its cyclic hemiacetal; when the pH is raised to the neutral or slightly basic range the di-aldehyde undergoes an aldol condensation with itself, followed by dehydration to generate α,β unsaturated aldehyde polymer. While both structures generate different mechanisms and products it is broadly agreed that the main reaction site for glutaraldehyde are the lysine or hydroxylysine residues of protein side chains. When crosslinking is carried out at pH3, Schiff base linkage of glutaraldehyde with two lysine residues is formed, that stabilises against acid hydrolysis.

At neutral pH, the Schiff base that forms with aldehyde is in conjugation with a double bond. It is the resonance interaction of the Schiff base with ethylenic double bond that leads to acid hydrolysis (as shown in Scheme 1).

Scheme 1

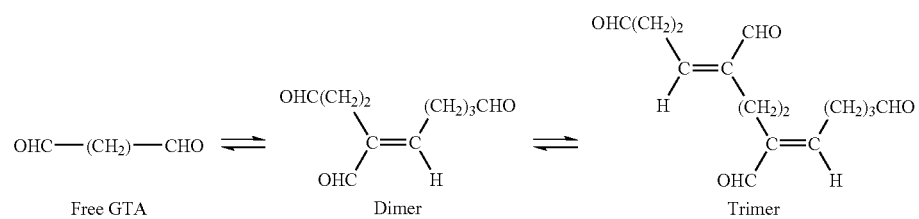

-continued

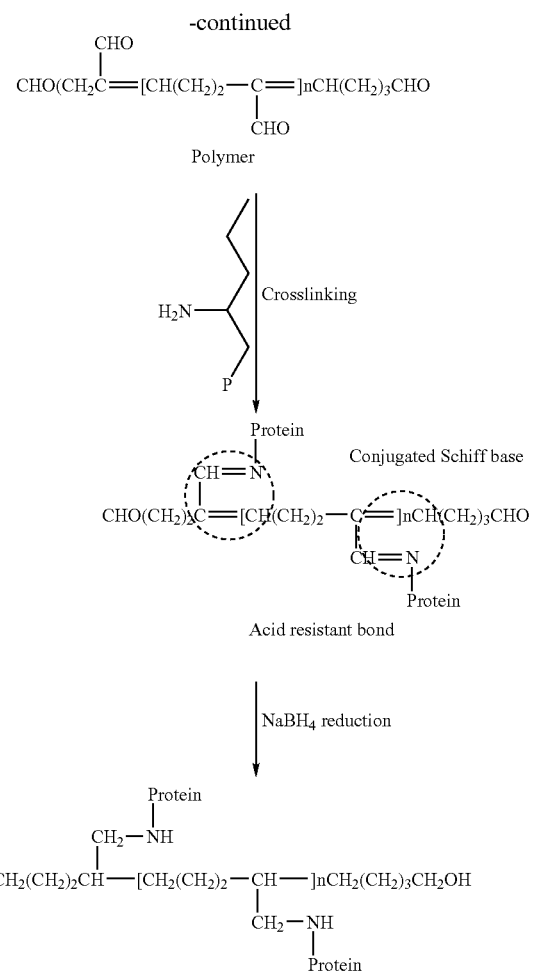

The conjugated Schiff base can still undergo Michael addition if the local amine concentration is particularly high. Alternatively, both acid or base catalyse the nucleophilic activity of aldehyde group, the cross-linking reaction with protein is also dependent on the availability of free ε-NH2 which is decided by $pK_a$ of lysine residue, or isoelectric point (pI) of the protein with media pH. In practice, the reaction is usually carried out at close neutral conditions such as pH 7.4 to achieve the optimal degree and rate of reaction. The resultant final stability of structure depends on the amount of glutaraldehyde used and the accessibility of reaction sites. Even so, competing reactions randomly occur by the various modes: mono-point fixation, bi-functional or multi-functional crosslinking, intermolecular or intra-molecular, etc. Hence, glutaraldehyde is an unconfined cross-linking reagent. Without being bound by theory, its success may be due to the diversity of molecular forms present simultaneously in the reagent solution, enabling bridging of different distances between reactive sites in protein tertiary structure, both by intermolecular and intra-molecular cross-links.

In one embodiment the process may additionally comprise the addition of a divalent or multivalent metal ion such as calcium (e.g. calcium chloride). The presence of calcium provides one or more of the following beneficial properties: (i) activation step of thrombin; (ii) gelation step of bulking agents such as alginate; (iii) control of the fibrinogen coagulation reaction; (iv) stability of cross-linked fibrinogen, fibrin or derived fragment to proteolytic degradation. It will be appreciated that the concentration of calcium will be selected such that it is sufficiently high enough to gelate alginate and/or activate thrombin, however, not exceed an amount which is likely leach from the composition and have cytotoxic effects. In one embodiment, calcium is added in a final concentration of between 1 and 50 mM. In a further embodiment, calcium is added in a final concentration of approximately 50 mM.

The washing step (c) is an essential process in order to remove the residual chemical cross-linking agent (and reducing agent if present), which may leach out over several hours or days. The washing step also increases biocompatibility of the resultant extracellular matrix compositions after cross-linking.

In one embodiment, the washing in step (c) is achieved using a suitable washing regime (e.g. 5×5 min washes) in a suitable buffer, such as PBS or a solvent, such as water, ethanol, methanol, propanol, isopropanol or a mixture thereof. In a further embodiment, the washing step (c) is accompanied by sonication. The presence of sonication in the form of ultrasound (e.g. 5×30 s bursts) further enhances the removal of the cross-linking agent (and reducing agent if present). In a yet further embodiment, the washing step (c) comprises 5×5 min washes in a mixture of ethanol/water (e.g. 95% v/v ethanol and 5% v/v water).

In one embodiment, the mixing step (a) may be achieved by foaming, e.g. mixing with aeration. In a further embodiment, foaming is achieved using an aerator (e.g. for 30 s).

In one embodiment, the mixture obtained in step (a) is cast, frozen and optionally lyophilised prior to the incubation step (b).

It will be appreciated that the casting step typically comprises procedures known to those skilled in the art of preparing extracellular matrix compositions. Typically, the casting step comprises incubation of the mixture obtained in step (a) at 37° C. for 15 minutes.

The freezing step will typically comprise storage of the cast mixture obtained in step (a) at below 0° C. (e.g. from −20° C. to −70° C.) from between several hours to overnight. In one embodiment, the cast mixture obtained in step (a) is frozen at −20° C. for 1 hour followed by freezing at −70° C. overnight.

It will be appreciated that the lyophilisation step typically comprises procedures known to those skilled in the art of lyophilisation. For example, lyophilisation of the cast, frozen mixture obtained in step (a) will typically comprise lyophilisation from between overnight to several days (e.g. 24 h) at a suitable pressure (e.g. $10^{-2}$ mBar) and at a suitable temperature (e.g. −60° C.).

In one embodiment, the washed, cross-linked composition obtained in step (c) is frozen and optionally lyophilised prior to use.

It will be appreciated that the freezing and lyophilisation steps may be performed as hereinbefore described.

According to a second aspect of the invention there is provided an extracellular matrix composition comprising cross-linked fibrinogen or a derivative thereof.

According to a third aspect of the invention there is provided an extracellular matrix composition obtainable by a process as hereinbefore defined.

In addition to the in vivo uses of the matrix composition defined herein, it is also envisaged that the composition may be beneficial for in vitro and ex vivo uses, such as tissue engineered models of skin for screening studies. Such models could be prepared by seeding fibroblasts and endothelial cells into the extracellular matrix composition and culturing keratinocytes on the upper surface.

According to a further aspect of the invention there is provided the use of an extracellular matrix composition as hereinbefore defined for in vitro, ex vivo or in vivo wound healing, tissue regeneration or as a tissue engineering scaffold.

According to a yet further aspect of the invention there is provided a method of wound healing or tissue regeneration which comprises application of an extracellular matrix composition as hereinbefore defined to a wound.

According to a yet further aspect of the invention there is provided an extracellular matrix composition as hereinbefore defined for use in wound healing tissue regeneration or as a tissue engineering scaffold in vitro, ex vivo or in vivo.

The invention will now be described, by way of example only, with reference to the accompanying drawings in which:

FIG. 1 demonstrates the results of an analysis of the effect of cross-linking upon resistance to proteolysis.

Figure 2:
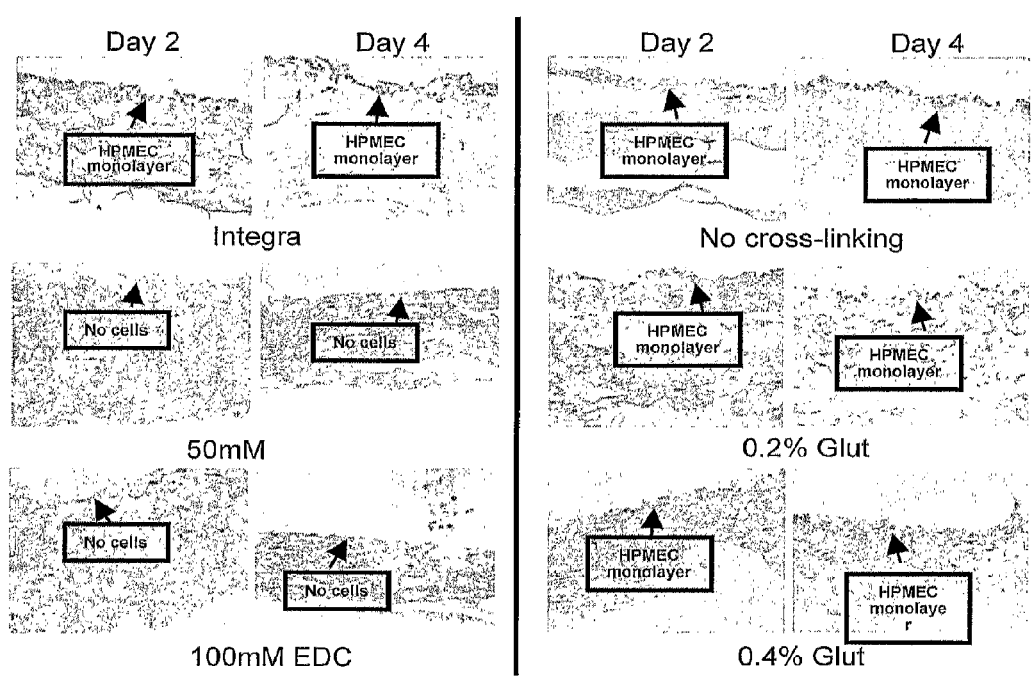
Figure 3:
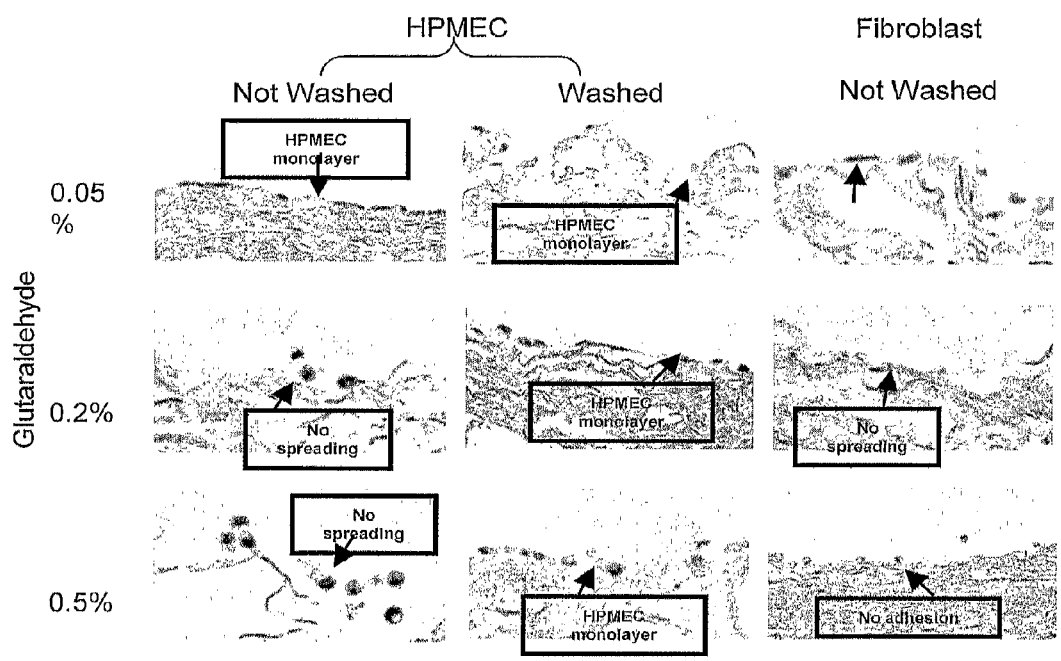
Figure 4:
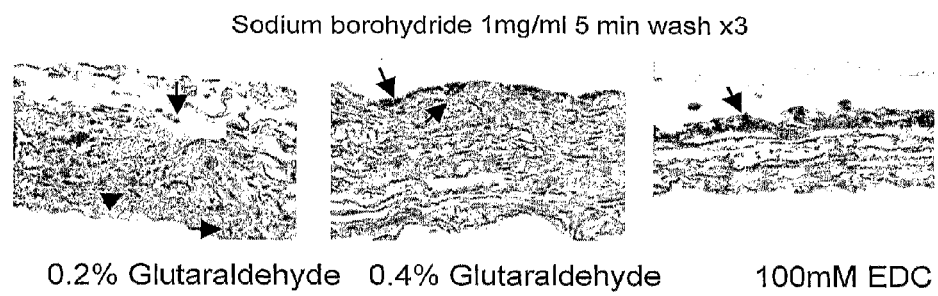

FIGS. 2-4 demonstrate the results of a biocompatibility analysis involving cross-linked scaffolds.

Figure 5:
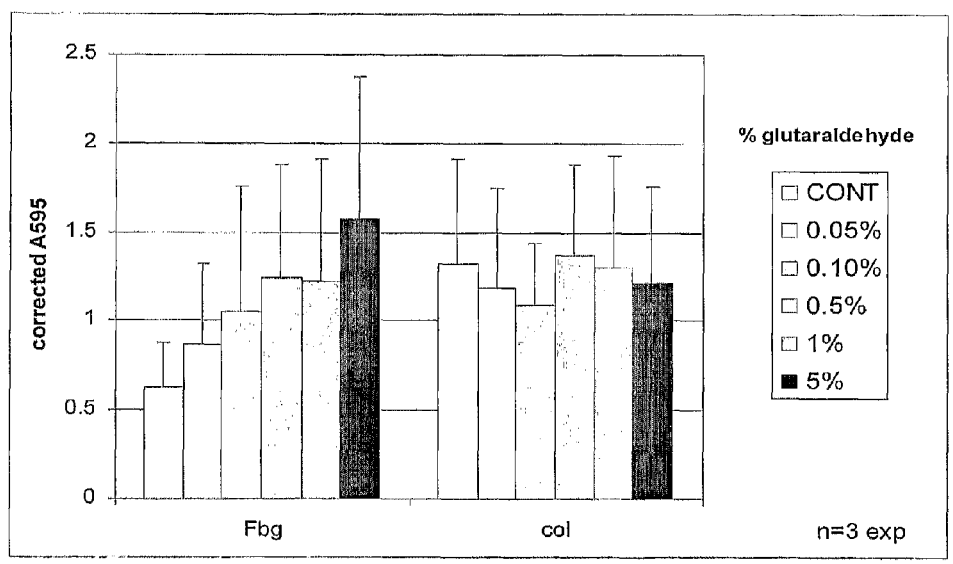

FIG. 5 demonstrates the results of an analysis of the effect of cross-linking upon cell adhesion.

Figure 6:
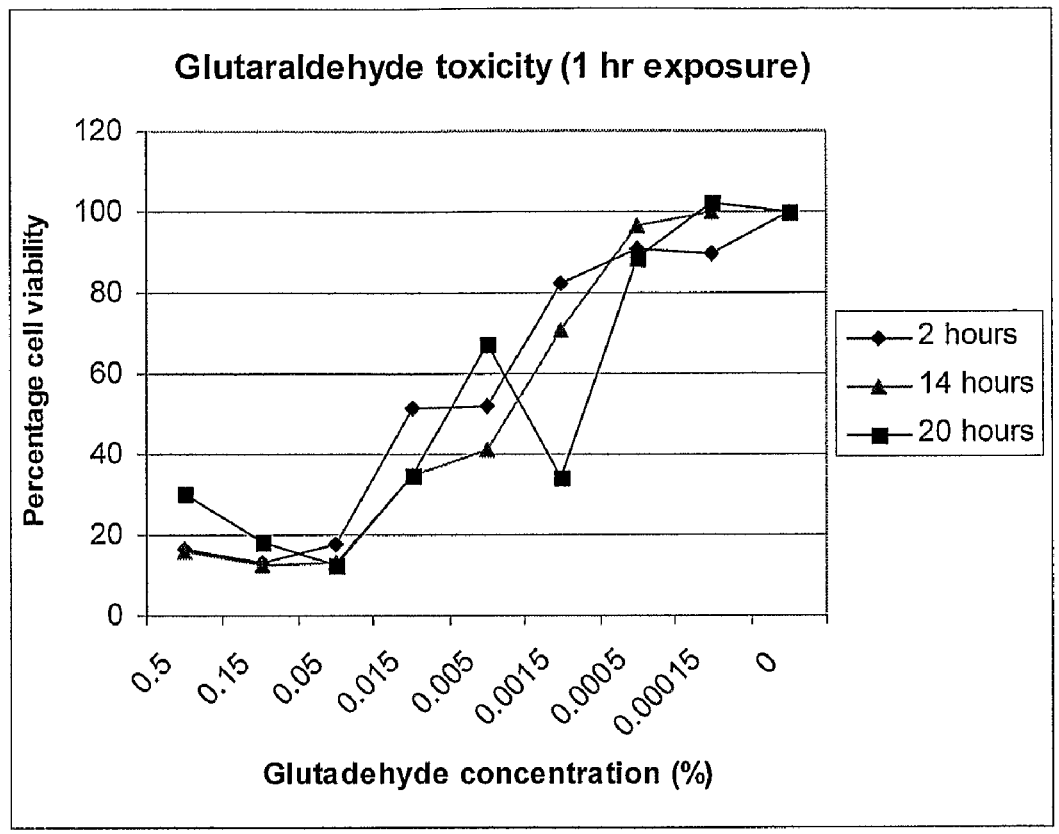
Figure 7:
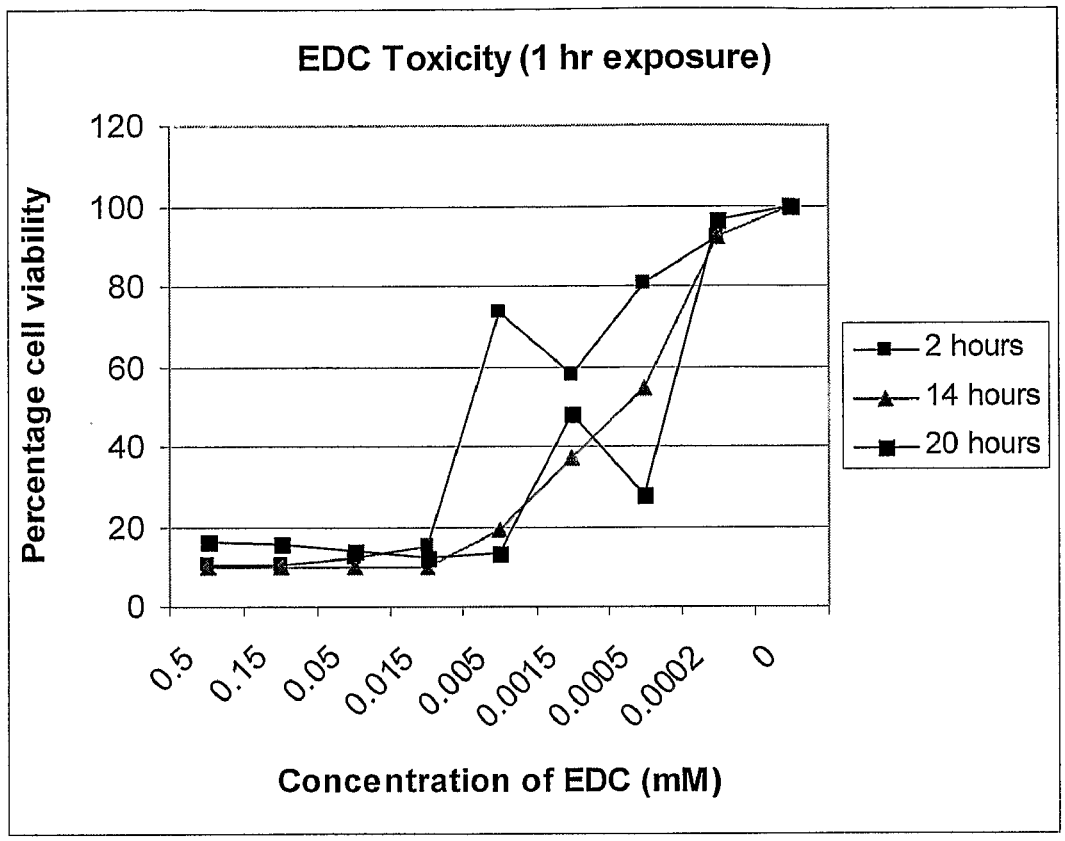
Figure 8:
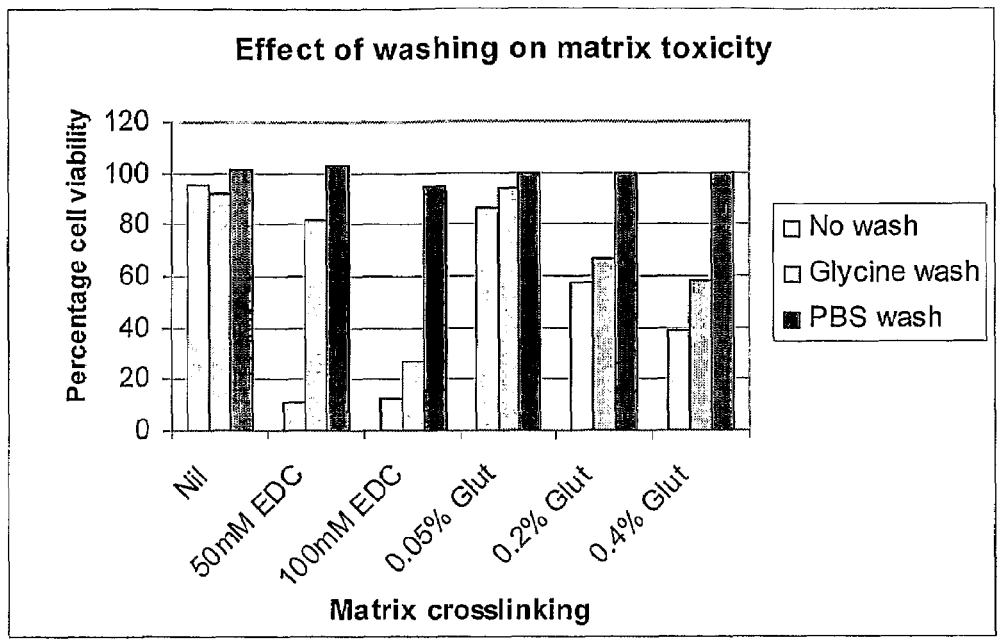

FIGS. 6-8 demonstrate the results of a toxicity analysis involving cross-linking agents.

FIGS. 9-12, 13-1 and 13-2 demonstrate the results of a fibrinogen flocculation/coagulation analysis.

FIGS. 14, 15A, 15B, 16A, 16B and 17-28 demonstrate the results of cross-linking optimisation studies.

FIGS. 29A and 29B demonstrates the results of an SEM analysis of fibrin/alginate scaffold.

FIGS. 30-35 demonstrate the results of a cytotoxic analysis of scaffold components.

FIGS. 36-41 demonstrate the results of an inflammatory analysis of scaffold components.

FIGS. 42A-42E demonstrates the results of an in vivo evaluation of a foam scaffold according to the invention.

EXAMPLES

Example 1

Preparation of an Extracellular Matrix Composition Comprising Fibrinogen Cross-Linked with Glutaraldehyde (a) Materials Used
2% Bovine fibrinogen (fraction 1-type IV-bovine plasma) (F4753, Sigma, St Louis, US) in PBS+$CaCl_2$/$MgCl_2$ (Gibco, Paisley, UK).
2% Alginic acid (Brown Algae, macrocystitis pyrifera mixed manuronic acid/guluronic acid polymer; Sigma) in Dulbecco's PBS, pH 7.4, solublised by addition of 1M NaOH.
Human thrombin (EC 3.4.21.5 human plasma T6884 Sigma) 10 NIHunits/ml in 0.1% BSA/M199 (Gibco, Paisley, UK).
25% Glutaraldehyde solution (Grade II G62517 Sigma).
1-(3-Dimethylamino-propyl)-3-ethyl-carbodiimide (EDC) HCl 98% (Acros Organics, New Jersey, USA).
Sodium borohydride (Sigma).
95% ethanol (Hayman Ltd, Witham, UK)/5% di$H_2O$.
Dulbecco's PBS without Calcium and Magnesium salts (PBS).
Dulbecco' PBS with Calcium and Magnesium salts.

(b) Equipment Used
Christ lyophiliser and vacuum pump (Vacuubrand RZ2.5 rated to $4 \times 10^{-4}$ mBar ultimate vacuum).
Polystyrene Petri dishes or multiwell plates.
Strippettes.
Autoclaved pipette tips.
Polypropylene tubes 50 ml.

(c) Matrix Preparation
A 2 ml fibrinogen solution was mixed with a 2 ml alginic acid solution in a 50 ml polypropylene tube at room temperature. To this mixture, a 50 μl thrombin solution was added and the resultant mixture was foamed using an aerator for 30 seconds. The foamed mixture was then cast in a 2.5×2.5 cm weigh boat followed by incubation for 15 min at 37° C. The cast mixture was then frozen for 1 hour at −20° C. followed by further freezing overnight at −80° C. The frozen product was then lyophilised for 24 hours using a Christ 1-2alpha lyophiliser at approximately $10^{-2}$ mBar and −60° C. The resultant product was then stored at 4° C. prior to transferring to a 6 well plate (Greiner-Bio, Germany). 10 ml glutaraldehyde (in a range of concentrations from 0.05-0.4%) in 95% ethanol/5% $H_2O$ was added to the substrate followed by incubation for four hours at room temperature. Following cross-linking, the substrate was washed five times in 10 ml 95% ethanol/5% $H_2O$ followed by freezing and lyophilisation as before and storage at 4° C. prior to further characterisation.

Example 2

Preparation of an Extracellular Matrix Composition Comprising Fibrinogen Cross-Linked with EDC This composition was prepared in an analogous manner to that described in Example 1 with the exception that 10 ml EDC (in a range of concentrations from 25-100 mM) was used as the cross-linking agent.

Example 3

Preparation of an Extracellular Matrix Composition Comprising Un-Cross-Linked Fibrinogen This composition was prepared in an analogous manner to Examples 1 and 2 with the exception that the cross-linking and washing steps were omitted.

Example 4

Preparation of an Extracellular Matrix Composition Comprising Fibrinogen Cross-Linked with Glutaraldehyde and Reduced This composition was prepared in an analogous manner to that described in Example 1 with the exception that the composition was hydrated after lyophilisation with 1% sodium borohydride for 5 minutes at room temperature. The composition was then drained and replaced with fresh reagent, incubated for a further five minutes, and then repeated (3 treatments in total). The resultant reduced composition was then washed with PBS five times, with five minutes soaking between each wash.

Example 5

Effect of Cross-Linking upon Proteolysis Resistance (a) Materials Used
Vivaspin 10 kDa cut off ultrafiltration tubes (0.5 ml).
ELISA plates.
Dulbecco's PBS.
2.5% Trypsin in PBS or versene.
Pierce BCA reagents A and B.
1 mg/ml BSA/PBS.
(b) Macroscopic Stability Method
Approximately 1 cm$^2$×2 mm thick sections of test scaffold as prepared in Examples 1, 2 and 3 (non-cross-linked or cross-linked with 50 or 100 mM EDC or 0.05%, 0.2% or 0.4% glutaraldehyde in 95% ethanol for 4 hours) were transferred to a polypropylene tube. 10 ml of 0.25% trypsin in PBS, or PBS alone (as control) was added to the tube which was then capped and incubated at 37° C. for 1 week.

The scaffold was then inspected for macroscopic integrity and the results were observed and recorded in Table 1 below:

TABLE 1

| Cross-Linking Agent | Treatment with PBS | Treatment with 0.25% trypsin |
|---|---|---|
| Control (No Cross-Linking Agent) | Fragmented | Degraded in 4 hours |
| 50 mM EDC | Intact at 1 week, remained at 3 weeks | Degraded in 24 hours |
| 100 mM EDC | Intact at 1 week, remained at 3 weeks | Degraded in 96 hours |
| 0.2% Glutaraldehyde | Intact at 1 week, remained at 3 weeks | Intact at 1 week, remained at 3 weeks |
| 0.4% Glutaraldehyde | Intact at 1 week, remained at 3 weeks | Intact at 1 week, remained at 3 weeks |

The results of Table 1 show that the fibrinous scaffolds were stable in PBS alone, however, there was partial solubilisation after several hours in the absence of cross-linking. The results also show that trypsin caused complete disintegration of non-cross-linked material of the control, however, EDC or glutaraldehyde cross-linked material were able to resist degradation. Glutaraldehyde was observed to be the most effective cross-linking agent for stabilisation.

(c) Quantitative Standardised Proteolytic Degradation Rate
Approximately 1 cm$^2$×2 mm thick sections of test scaffold as prepared in Examples 1, 2 and 3 (cross-linked with 50 or 100 mM EDC or 0.05%, 0.2% or 5% glutaraldehyde) along with a commercially available extracellular matrix composition (Integra™) was transferred to a polypropylene tube. 10 ml of 0.25% trypsin in versene, or versene alone (as control) was added to the tube which was then capped and incubated at 37° C. for up to 48 hours.

At specified intervals (e.g. 0, 2, 4, 24 and 48 hr), 100 µl samples were removed and transferred to a vivaspin tube, and centrifuged at 8,000 g for 10 minutes. The ultrafiltrate was then recovered and 10 µl aliquots of each sample were pipetted to a 96 well microtitre plate in triplicate.

A 1 mg/ml BSA in PBS standard calibration solution was prepared, and from this a standard dilution series of 0, 1.25, 2.5, 5, 10, 20 µg/ml in PBS was prepared. 10 µl of each calibration solution was pipetted in triplicate.

A working BCA solution (50 parts A+1 part B) was prepared and 200 µl of this solution was added to each well followed by incubation at 37° C. for 1 hr. The plate was then cooled to room temperature and read at 540 nm. The sample protein concentration was then calculated from the standard using a spreadsheet and the results are shown in FIG. 1.

The quantitative proteolytic degradation analysis shown in FIG. 1 corroborate the results obtained with the macroscopic stability assessment shown in Table 1 above. For example, EDC cross-linked matrices showed rapid release of high levels of peptides. Intermediate glutaraldehyde cross-linking (0.05% and 0.2%) showed more stability and matrices having 5% glutaraldehyde demonstrated only minimal release of degradation peptides, which was comparable to the commercially available extracellular matrix composition (Integra™).

Example 6

Effect of Cross-Linking Upon Biocompatibility (a) Materials Used
Dulbecco's PBS w/o Ca & Mg AND with Ca & Mg, pH 7.4.
Minimal Media M199+0.5% BSA.
Trypsin (0.25% solution in versene/PBS).
5% Agarose in PBS (without Ca/Mg).
4% paraformaldehyde in PBS (PFA/PBS).
(b) Equipment Used
24 well plates.
Sterile conical bottom capped 50 ml polypropylene tubes.
Sterile 25 ml polystyrene universal tube.
Strippettes.
autoclaved pipette tips.
Stainless steel culture cylinders inside dia=9 mm, outside dia=1.2 mm, height=10 mm.
(c) Scaffold Attachment
The test scaffolds as prepared in Examples 1, 2 and 3 along with a commercially available extracellular matrix composition (Integra™) were cut into approx 1.2 dia×2 mm disks. Each scaffold was transferred into a separate well of a 24-well culture plate. Agarose solution was melted at around 80° C. and droplets of around 20 µl were pipetted to the edges of the scaffold to glue the scaffold onto the well surface.

The test gel was hydrated with culture medium and a culture cylinder was placed centrally on top of the scaffold material to create an inner well.

(d) Cell Types

Materials: Culture media.

Foetal bovine serum (Gibco-Invitrogen) was heat inactivated by incubation at 56° C. for 30 minutes (HIFBS).

Platelet-depleted plasma derived foetal bovine serum (PD-PDS) was obtained from First Link (Birmingham, UK).

Medium 199 with Earles Salts and 25 mM HEPES was supplemented with 200 µM Glutaminyl-alanine+100 U/ml Penicillin/100 µg/ml Streptomycin/100 µg/ml Ceftazidine (M199).

Standard HPMEC growth medium was M199+5% PDPDS+2% HIFBS and HPMEC high growth medium was M199+5% HIFBS.

Dulbecco-modified Eagles Medium with 1% glucose was supplemented with 100 U/ml Penicillin/100 µg/ml Streptomycin/100 µg/ml Ceftazidine (DMEM).

HDF growth medium was DMEM+10% HIFBS.

Human Placental Microvascular Endothelial Cells (HPMEC)

HPMEC were isolated from human placentae obtained with consent and cultured according to previously published methods (Leach et al. (1994) *Placenta* 15(4): 355-64; Dye et al. (2001) *Microvasc Res* 62(2): 94-113; Dye et al. (2004) *Faseb J* 18(1): 125-7). Established cultures are phenotypically stable for typically up to 25 passages at a split ratio of 1:3. Cultures are maintained in standard growth medium (M199+5% PDPDS+2% HIFBS). Cultures were maintained in a humidified 5% CO2 and 37° C. atmosphere. For biocompatibility assessment of scaffolds, harvested cells were resuspended in high growth medium (M199+5% HIBFS). For cell adhesion assays harvested cells were resuspended in M199+0.5% BSA.

Human Dermal Fibroblasts (HDF)

Human dermal fibroblasts were isolated from normal adult human skin obtained from routine operative excisions with patient consent. Specimens were maintained under sterile conditions while subdermal fat was removed by dissection and skin was cut into approximately 1-2 mm$^3$ pieces. These were introduced into T25 culture flasks using sterile forceps (6 per flask) dermal side down, and 3 ml culture medium was introduced. HDF Growth medium is DMEM+10% HIFBS. Cultures were maintained in a humidified 5% CO2 and 37° C. atmosphere for around two to three weeks to allow egress of fibroblasts. The skin explants were then removed and cultures maintained for a further 1-2 weeks before passage. Thereafter, cultures were maintained by passaging at around 1:4 split ratio, and were used up to around passage 9 or 10. For biocompatibility assessment of scaffolds, harvested cells were resuspended in growth medium (DMEM+10% HIBFS). For cell viability and cytotoxicity assays, cells were resuspended with DMEM+2% HIBFS as described.

(e) Cell Preparation 0.25% Trypsin/versene was prepared from tissue culture stocks, and warm culture medium and PBS without Ca/Mg was warmed to 37° C.

The growth medium was aspirated from confluent cells. The culture was rinsed with PBS and aspirated. Trypsin/versene (1 ml per 25 cm$^3$) was added and the culture was incubated at 37° C. until detachment of the cells. An equal volume of culture medium was added to the cell suspension and transferred to a universal tube. The culture flask was washed out with PBS and then transferred to the universal tube. Centrifugation was then performed at 200×g for 7 minutes, the supernatant was aspirated and the cells were resuspended in 1-2 ml culture as appropriate, titurated, and cell density was counted (1:10 in 4% trypan blue/PBS), aiming for around 2×10$^6$/ml.

The number of cells required for the assay was calculated using 0.5-1×10$^5$ cells/well. The calculated volume of cells was diluted to the total assay volume based on 500 µl/well in M199/BSA.

(f) Biocompatibility Assessment Assay

The scaffold hydration medium was aspirated from each well and replaced with 1 ml fresh culture medium.

The cell suspension (5×) was titurated to ensure an even suspension and 500 µl/well was aliquoted dropwise onto the scaffold in the inner well.

The plates were covered and incubated in a humidified atmosphere at 37° C., 5% CO$_2$ for up to 4 days.

The culture medium was aspirated, cells were fixed in 4% PFA/PBS for 15 min, washed twice in PBS and 5% LMP agarose was added dropwise and allowed to set. The agarose-embedded scaffold was gently removed from each well, the region within the culture ring was separated, excess agarose was trimmed off and placed between two sponges in a tissue processing basket for automated wax embedding (Bright).

The embedded specimen was bisected and mounted on a microtome block with side-on orientation. The blocks were section at 8 µm, and stained with Haematoxylin & Eosin.

Further sections were retained for immunostaining with Ki67 proliferation antigen and observed by bright field microscopy. The results were recorded and representative photomicrographs were taken with a Leica DC200 digital camera and frame-grabbing software which are shown in FIGS. 2-4.

The results shown in FIG. 2 demonstrate that endothelial cells exhibited differing degrees of adhesion to glutaraldehyde or EDC cross-linked fibrin/alginate matrices washed out 5 times in 95% ethanol, compared to non-cross-linked fibrin/alginate matrices. Endothelial cells were observed to adhere to glutaraldehyde cross-linked matrices but appeared inhibited, and on EDC matrices they failed even to adhere. These results demonstrate that stabilising concentrations of cross-linking agents have persistent adverse effects. On a parallel reference (Integra™ material) the same cells formed a typical endothelial monolayer, but failed to ingress into the matrix.

The results shown in FIG. 3 demonstrate that endothelial cells exhibited adhesion and spreading to 0.2% and 0.5% glutaraldehyde-cross-linked fibrin/alginate matrices which were further washed with PBS after the second lyophilisation. The fact that both endothelial cells and dermal fibroblasts failed to spread on 0.2% and 0.5% glutaraldehyde-cross-linked matrices without the further PBS wash step indicated that the failure to spread is not specific to endothelial cells.

The results shown in FIG. 4 demonstrated that endothelial cells exhibited adhesion and spreading on borohydride-reduced fibrin alginate matrices cross-linked by either glutaraldehyde or EDC. Furthermore, endothelial cells ingressed rapidly into a borohydride-reduced 0.2% glutaraldehyde cross-linked fibrin alginate matrix. This behaviour markedly contrasts with the same cells on the reference collagen-based Integra™ material and is expected to translate in vivo to rapid angiogenesis.

Example 7

Effect of Cross-Linking upon Cell Adhesion (a) Materials Used

NaHCO$_3$ 0.1M pH 9.5 Also, 0.1% BSA in NaHCO$_3$.

Versene solution for tissue culture.

Dulbecco's PBS w/o Ca & Mg AND with Ca & Mg, pH 7.4.
Minimal Media M199+0.5% BSA (M199/BSA).
Accutase (1× solution stored in aliquots −20° C., Innovative Technologies Inc).
Fibrinogen (bovine, Sigma).
Fibrin E fraction (approx 1 mg/ml in PBS, 100 U/ml trasylol).
Fibronectin (bovine, Sigma).
Collagen type I, mg/ml in 0.6% acetic acid (First Link, Birmingham).
Crystal violet stain solution (0.5% crystal violet, 1.85% formaldehyde, 0.85% NaCl, 50% EtOH).
PBS w/o Ca & Mg for washing (make up from 10× stock).
Acetic acid, 33%.
25% Glutaraldehyde aqueous solution (Sigma).
EDC (Acros).

(b) Equipment Used

CovaLINK 96 well plates.
Sterile conical bottom capped 50 ml polypropylene tubes.
Sterile 25 ml polystyrene universal tube.
Strippettes.
Autoclaved pipette tips.
ELISA spectrophotometer plate reader.

(c) Matrix Coating and Cross-Linking

Fibrinogen was dissolved at 1 mg/ml in PBS, which required warming from 20-37° C. The test matrix proteins were diluted into cold (0-4° C.) 0.1M NaHCO$_3$ pH 9.5 and 50 µl per well was pipetted into Nunc covalink 96 well ELISA plates and incubated for 1 hr at 37° C. Quadruplicate wells were allocated for each cell treatment or positive control, and wells for 'null' adhesion received BSA coating only. All samples were incubated for 1 hr at 37° C.

A working solution of cross-linking agent was prepared and a range dilution (0.05, 0.1, 0.5, 1, 5% glutaraldehyde; 0.3, 1.5, 6, 25 100 mM EDC). Protein solution was aspirated from the well and 100 µl/well of cross-linking solution was pipetted followed by incubation for 1 hr at 20° C.

The well was washed with a sufficient number of washes to reduce residual concentration to below cytotoxic limits (5×100 µl per well) with PBS, replaced with 50 µl/well BSA/NaHCO$_3$ (covalent reagent blocking step) and incubated for 1 hr at 37° C. Washing was performed twice with sterile PBS and the plate was stored with 100 µl/well PBS until the cells were ready.

(d) Cell Preparation

Accutase was thawed and M199/BSA was prepared. The growth medium was aspirated from confluent cells, the culture was rinsed with versene and aspirated. Accutase (1 ml per 25 cm$^3$) was added and the culture was incubated at 37° C. until detachment of cells. An equal volume of M199/BSA medium was added to the cell suspension and transferred to a universal tube. The culture flask was washed out with PBS, transferred to the universal tube and centrifuged at 200×g for 7 minutes. The supernatant was aspirated and the cells were resuspended in 1-2 ml M199/BSA as appropriate, titurated, and cell density was counted (1:10 in 4% trypan blue/PBS), aiming for around 2×10$^6$/ml.

The number of cells required for the assay was calculated using 1-2×10$^4$ cells/well. The calculated volume of cells was diluted to the total assay volume based on 100 µl/well in M199/BSA.

(e) Cell Adhesion Assay

The cell suspension (5×) was titurated to ensure an even suspension and 100 µl/well was aliquoted into the pre-coated wells. The plate was covered with a plate seal adhesive film and incubated in a humidified atmosphere at 37° C., 5% CO$_2$ for 1 hr.

The culture medium was aspirated, the wells were gently washed twice with 100 µl PBS, using fine needle vacuum manifold to aspirate/wash. Adherent cells were fixed/stained with 50 µl crystal violet solution and incubated for 10 minutes.

Crystal violet was aspirated using a fine needle and a dedicated crystal violet aspirator flask. The wells were washed twice with 400 µl PBS, using a fine needle manifold to drip the solution onto the side wall whilst holding the plate at 45° and flicking to void the wells and draining by inversion onto paper towel. It is important to remove any residual crystal violet from the neck of each well which may not have been washed away after the first wash with cotton buddie.

The bound Crystal Violet stain was dissolved with 33% acetic acid, the plate was tapped until all the crystal violet was evenly dissolved in each well and checked carefully before reading. The OD was measured with a microplate reader at 595 nm. Cell adhesion (ie number of cells remaining) is proportional to ($A_{595}$[test substratum]-$A_{595}$[BSA]). Adhesion of test condition was expressed as a fraction of adhesion to corresponding control substratum and the results are shown in FIG. 5.

The results shown in FIG. 5 surprisingly demonstrate that cross-linking continuously increases adhesion to fibrinogen but has a biphasic effect upon collagen.

Example 8

Toxicity Analysis (a) Materials Used

Growth medium: Dulbecco-modified Eagles medium (DMEM) with 10% HIFBS (heat-inactivated fetal bovine serum).
Dulbecco's PBS.
2.5% Trypsin in PBS, stored in aliquots at −20° C.
Versene (NaEDTA/PBS).
MTS (3-(4,5-dimethylthiazol-2yl)-5-(3-carboxymethoxyphenyl)-2-(4-sulphophenyl)-2H-tetrazolium, inner salt, Promega) 2.14 mg/ml in PBS, 20 ml aliquots, stored at −20° C.
PMS (phenazine methosulphate, Sigma) 0.9 mg/ml in PBS, 2 ml aliquots, stored at −20° C.

(b) Equipment Used 24 well culture plates.
ELISA spectrophotometric plate reader.

(c) Cell Preparation

Culture medium was aspirated from confluent culture and washed with versene. 1 ml 0.25% trypsin/versene was added per 25 cm$^2$ and incubated at 37° C. until detached. Trypsin was neutralised with an equal volume of growth medium, the cell suspension was transferred to a universal tube. The culture flask was washed with PBS and transferred to the universal tube. Centrifugation was performed at 200×g for 7 minutes. Cells were resuspended in 1-2 ml growth medium.

Cells were seeded (10$^5$/well) into 24-well plates in 0.5 ml DMEM growth medium/well and incubated at 37° C. in a humidified 5% CO$_2$ incubator, until the cells adhered and spread, typically overnight. A single well blank/plate was retained for a reagent control.

(d) Toxicity Assay

Culture medium was aspirated from cultures and replaced with: a weighed sample of scaffold (20 mg/well) in fresh serum-free DMEM; serum-free DMEM with a range of dilutions of glutaraldehyde or EDC as cross-linking agents. Cells were incubated at 37° C. in humidified 5% CO$_2$ for 1 hr.

The medium and scaffold material was removed from cells and replaced with fresh maintenance medium (DMEM with 2% HIFBS) and returned to the incubator for 2 to 22 hours. Direct toxicity measurements were taken at 2, 14 and 20 hours. For exposure to matrices, incubation was for 20 hrs. The same medium was added to an empty control well for a reagent blank.

(e) MTS/PMS Assay of Cell Viability

Aliquots of MTS & PMS stock solutions were thawed and a working MTS/PMS reagent was prepared (2 ml MTS+100 µl PMS). MTS/PMS reagent was added to all wells (50 µl/well) and returned to the incubator for 2-4 hours, until colour developed in the medium over control cultures without toxic challenge.

100 µl aliquots of medium were transferred to a 96 well ELISA plate for spectrophotometric measurement at 495 nm.

The blank absorbance was subtracted from all readings and the results (test—blank) were expressed as a percentage change from the test positive control.

The results of the toxicity analysis are shown in FIGS. 6-7 were it can be generally seen that acute exposure of human dermal fibroblast cultures to glutaraldehyde or EDC results in acute concentration-dependent toxicity. Incubation of cells for up to 24 hr after a period of exposure shows that the loss of viability is similar after 2 hr or 20 hr and does not indicate that any delayed death, which could be due to induction of apoptosis for example, is a major process.

The LD50 for cells is a factor of 5-10 times less than the lowest cross-linking concentration of glutaraldehyde, but is 5,000-10,000 times less than the lowest concentration of EDC used.

(f) Effect on Toxicity of Washing

Matrices of 1% fibrin/1% alginate, foamed & lyophilised, were cross-linked with EDC or glutaraldehyde and washed 5 times in glycine or PBS before a second lyophilisation, or not, as indicated. 20 µg pieces of matrix were incubated in wells with confluent fibroblast cultures in serum-free medium for 1 hr to detect leachable toxicity, assessed after 20 hr to check for induction of delayed cell death.

The results of the washing analysis may be seen in FIG. 8 wherein matrices which were not washed had demonstrable leachable toxicity. The preferred wash procedure with five changes of PBS proved to be effective in removing any residual leachable toxicity from cross-linked matrices. PBS was more effective than 1 mM glycine, pH 7.4.

Example 9

Flocculation Analysis Involving Fibrinogen (a) Materials Used
PBS (without Ca/Mg) pH 7.4.
HEPES buffered saline (5 mM HEPES, 150 mM NaCl, pH7.4.
10% Bovine fibrinogen solution (wt/vol) in PBS (w/o Ca/Mg) pH 7.4 (prepared by dissolving by gentle mixing and warming to 37° C., pH corrected with 0.3M NaOH, then stored on ice).
10% Sodium alginate solution in PBS (w/o Ca/Mg) pH 7.4 (prepared by dissolving alginic acid slurry by dropwize addition of 10M, then 1 M NaOH).
10 U/ml human thrombin (Sigma) in M199/0.1% BSA.
20% Polyethylene glycol (MW=20,000 and 6,000; BDH) in PBS (without Ca/Mg), pH 7.4.
20% Viastarch (Fresenius) in PBS (w/o Ca/Mg), pH 7.4.
20% BSA (Sigma) in PBS (w/o Ca/Mg), pH 7.4.

(b) Equipment Used
Spectrophotometer.
Disposable optical cuvettes (1 ml).

(c) Assessment of Fibrinogen Coagulation or Flocculation

Fibrinogen, PBS or HEPES-saline and alginate, PEG or viastarch or thrombin or calcium chloride were mixed at desired concentrations up to a final volume of 1 ml in a cuvette, rapidly mixed by gentle inversion using parafilm, and transferred to the spectrophotometer to read the OD. Because alginate has significant colour, alginate-only dilutions at each test concentration were prepared as spectrophotometer blanks. Example experiments were performed at room temperature.

(d) Rate Measurements

For reaction rate studies, 100 µl alginate, 10 µl thrombin and appropriate volume of diluent to give a final volume of 1 ml were mixed in the cuvette. For experiments involving addition of $CaCl_2$, 100 µl of fibrinogen and 10 µl of 1 M $CaCl_2$ were mixed in a 0.5 ml vial. At t=0, fibrinogen was pipetted into the cuvette of alginate/thrombin, the tube was rapidly mixed by inversion using parafilm sealant, and placed in the spectrophotometer for a first reading at 30 seconds. Three cuvettes were studied in parallel with this method.

Figure 9:
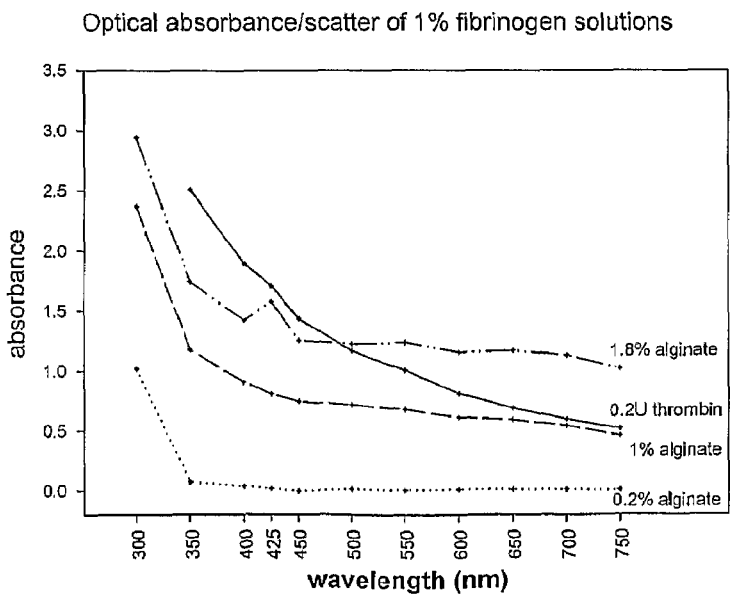

The flocculation results are shown in FIGS. 9 to 14. FIG. 9 demonstrates concentration-dependent flocculation of 1% fibrinogen by 1% or 1.8%, alginate which gave a similar optical scattering to coagulation induced by 0.2 U thrombin. 0.2% alginate failed to cause measurable turbidity. Optical measurements at 425 nm enabled the effects of concentration of different components on fibrinogen precipitation to be measured. The inherent tendency of fibrinogen (but not for example serum albumin) to flocculate or 'pseudo-coagulate' is of potential utility in forming scaffold structures, either by aeration or forming methods or by fibre extrusion. Flocculation and coagulation is reflected by light scattering across the visible light spectrum, and can be measured spectrophotometrically (as in FIG. 9). The rate of flocculation at room temperature is rapid and is essentially complete after several seconds of vigorous mixing.

Figure 10:
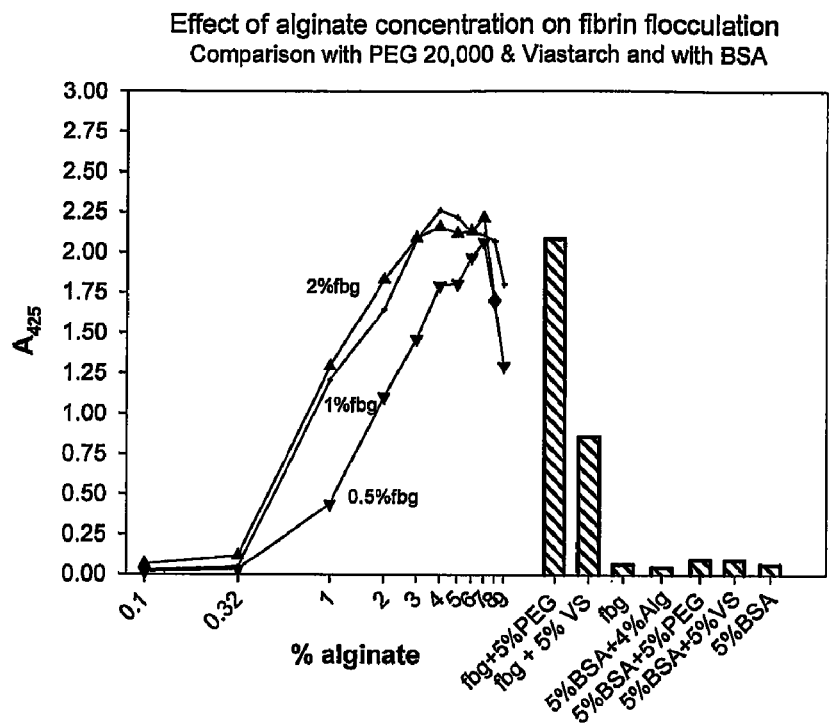

FIG. 10 further demonstrates the concentration-dependent flocculation of fibrinogen at 0.5%, 1% and 2% with alginate over the range 0.1-9%, in PBS diluent. This figure also shows that polyethylene glycol 20000 (PEG) and hydroxyethylstarch (viastarch, VS) cause similar flocculation. This effect is specific for fibrinogen since BSA at concentrations up to 10% was not flocculated by 4% alginate, 5-10% PEG or 5% viastarch. The flocculation reaction clearly depends on the concentration of alginate and fibrinogen, but not in a direct reciprocal relationship. The concentration dependence curves in FIG. 10 show a threshold alginate for flocculation, and a decrease in the alginate required for maximal flocculation with higher fibrinogen concentrations.

Figure 11:
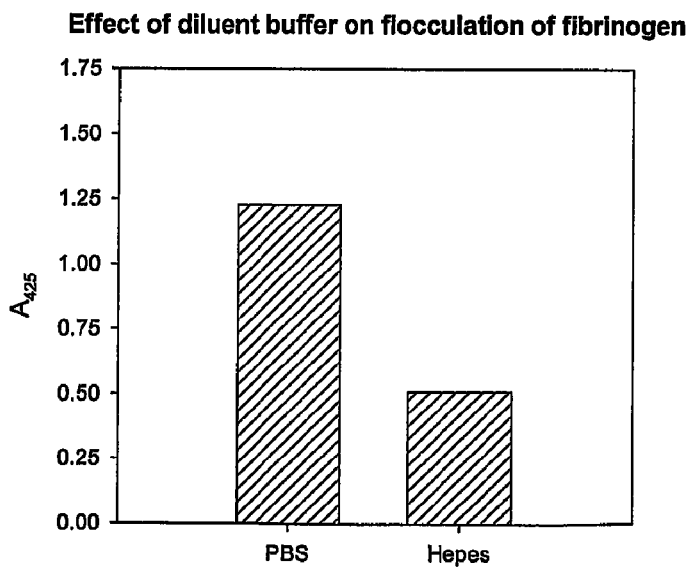

FIG. 11 demonstrates that the buffer system for fibrinogen/alginate mixture has a significant influence on the extent of spontaneous flocculation, shown for 1% fibrinogen mixed with 1% alginate in isosmotic buffer at pH7.4. Phosphate buffered saline resulted in greater flocculation than HEPES. Therefore, flocculation in alginate is influenced by the buffer composition. For example, use of HEPES-saline as a diluent in place of PBS gave a reduced flocculation in FIG. 11.

Figure 12:
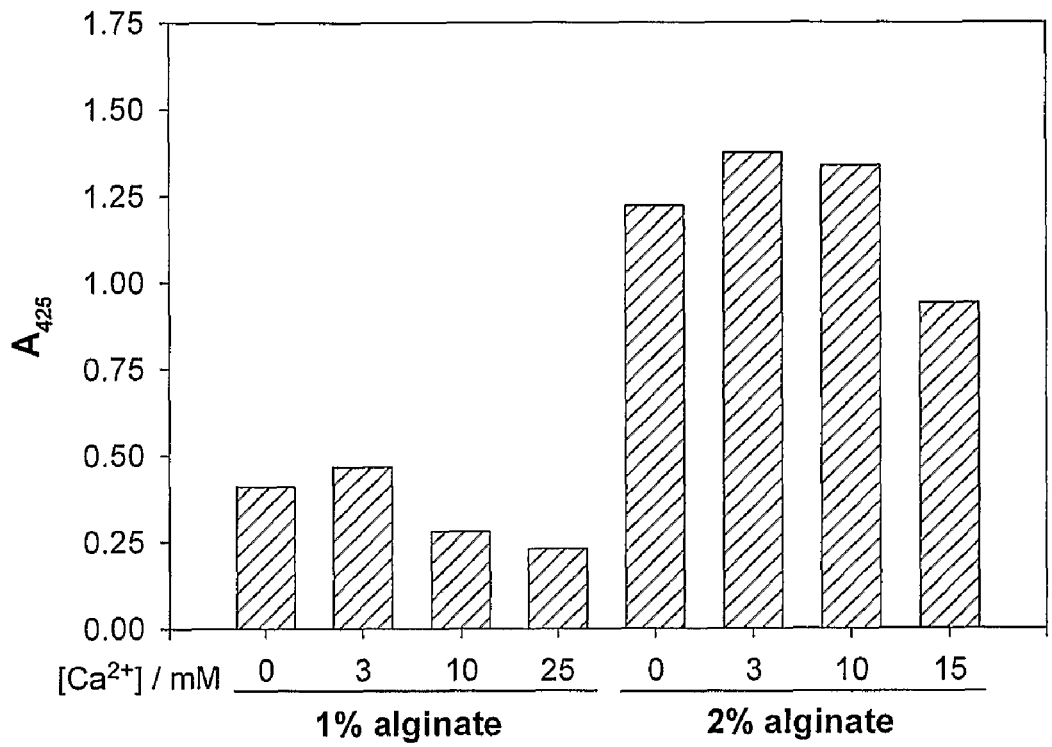

FIG. 12 demonstrates that calcium ions modulated the alginate flocculation of 1% fibrinogen. Calcium concentrations sufficient to induce viscosity increase and gelling of alginate (<10 mM) reduced the flocculation density. The effect of calcium in controlling flocculation and enzymic coagulation is therefore likely to provide a useful means of controlling fibrin deposition. Calcium addition to fibrinogen/ alginate mixtures can modulate the spontaneous flocculation, as exemplified in FIG. 12. Calcium ions increased the rate of thrombin coagulation, and density of coagulum, in the absence of alginate. By contrast calcium ions with alginate attenuate the rate of coagulum formation, exemplified in FIG. 13.

Figure 13:
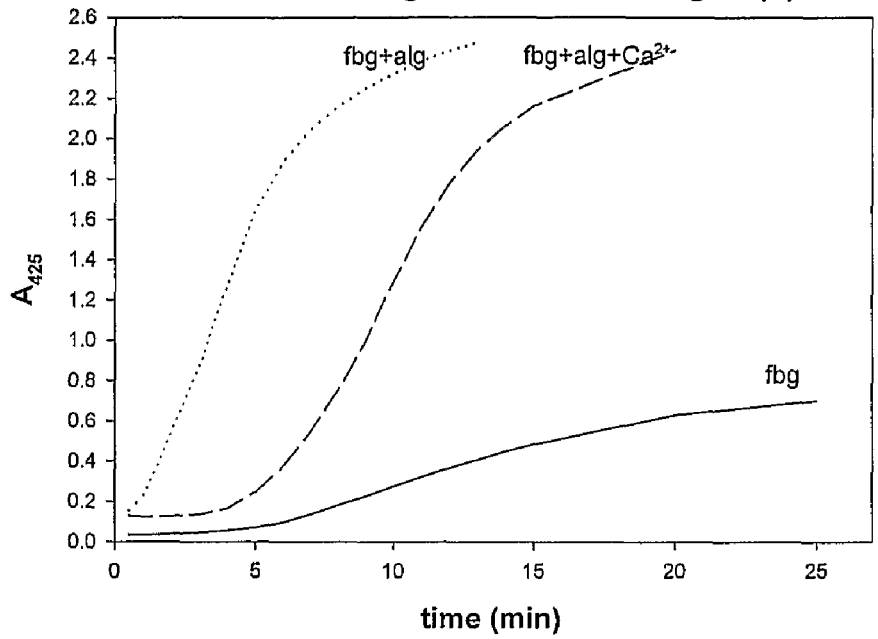
Figure 13:
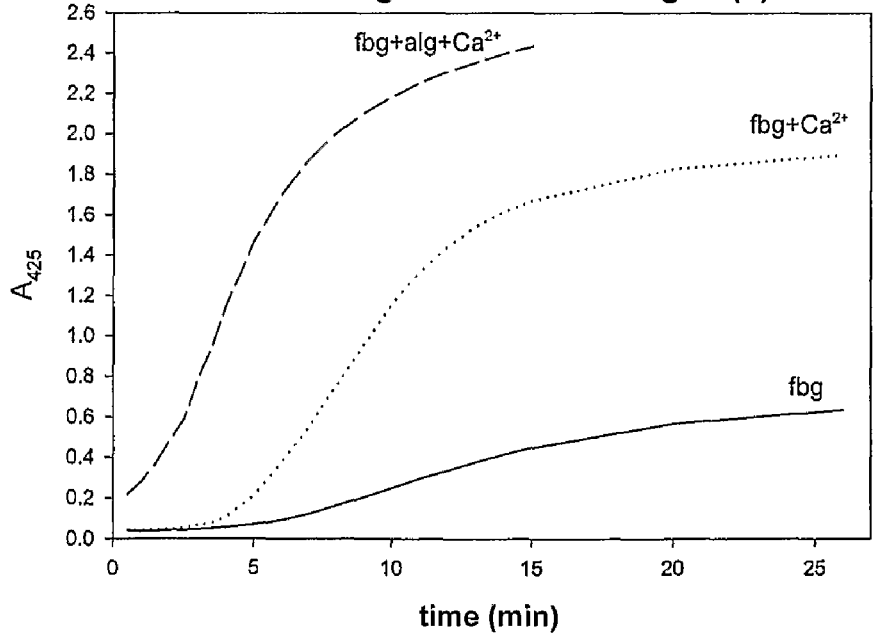
Figure 14:
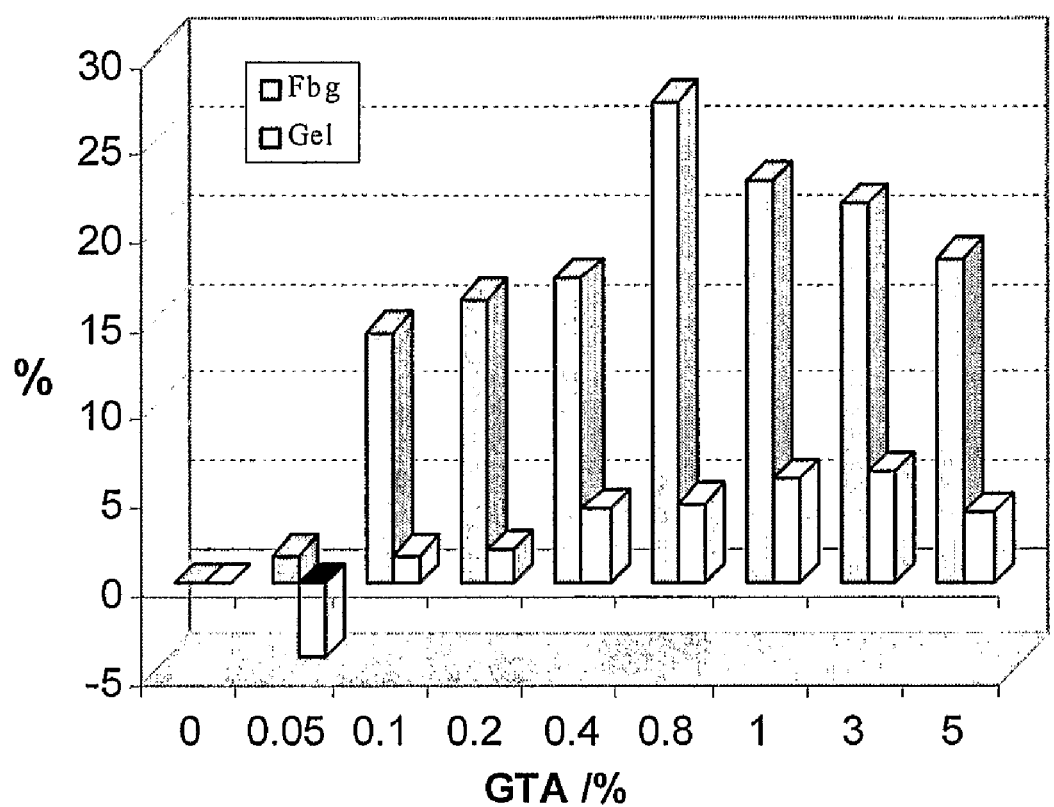

FIG. 13 demonstrates that 1% alginate increased the rate of 1% fibrinogen coagulation catalysed by 0.1 U/ml thrombin and density of clot, but addition of 10 mM $Ca^{2+}$ to alginate attenuates the rate increase, without effecting the final density. The same concentration of calcium increased the rate and density of thrombin coagulation of fibrinogen in the absence of alginate, but to a lesser extent. Therefore, alginate appears to accelerate thrombin coagulation, and results in formation of a denser clot. The enzymic coagulation process appeared to compete with the flocculation process, resulting in a progressive formation of a coagulum rather than instantaneous flocculum, as shown in FIG. 13. Thrombin added to a flocculum resulted in its coagulation.

Example 10

Cross-Linking Optimisation Studies (a) Materials Used
2% bovine fibrinogen (fraction 1-type IV-bovine plasma) (F4753, Sigma, St Louis, US) in $H_2O$ (prepared by dissolving in $H_2O$ and incubation at 40° C. for 1 h).
2% Gelatin (Bovine skin, 225 Bloom, type B, Sigma) in $H_2O$ (prepared by dissolving in $H_2O$ and incubation at 70° C. for 1 h).
25% glutaraldehyde solution (Grade II G62517 Sigma).
sodium borohydride (Sigma)
morpholinoethane sulphonic acid (MES) (Sigma) buffer 100 mM pH 7.4
ethanol (Hayman Ltd, Witham, UK)
hydrochloric acid (BDH)
2,4,6-trinitrobenzenesulfonic acid (Sigma)
25 mg/ml Trypsin (Bovine pancreas) in PBS (Invitrogen)
BCA™ protein Assay (Pierce)
Phenol (Sigma)
70% perchloric acid
(b) Equipment Used
Plastic square weigh-boats (35×35×9 mm)
Dry heat block (Techne Dri-Block DB 3D)
UV-Vis spectrometer (Camspec M330)
Microplate reader (Biorad)
Differential scanning calorimeter (TA, 1000)
Fourier Transform Infrared spectrometer (Shimadzu 8400 s)
(c) Preparation of Cross-Linked Protein Film Batches of 2 ml of 2% fibrinogen or 2% gelatin were cast in plastic square weigh-boats (35×35×9 mm). Film was obtained after overnight air-drying in a fume hood. The protein content in one film is about 26 mg for fibrinogen and 40 mg for gelatin. The glutaraldehyde cross-linking reaction was carried out in 100 mM MES pH 7.4/80% Ethanol/20% $H_2O$ (v/v) buffer (unless specified). Commercial 25% (w/w) glutaraldehyde solution was diluted into the buffer at the serial concentrations of 0.05%, 1%, 2%, 4%, 8%, 1%, 3%, 5% (v/v). 2 ml cross-linking solution was used in one weigh-boat for one film. The reaction was carried out in the weigh-boat, covered, with constant shaking at 23° C. for 4 hours (unless specified).

Films were thoroughly washed in 15 ml $H_2O$ for 5 min, 10 times; or washed in 0.1% $NaBH_4$ aqueous solution 15 ml for 5 min, 5 times, followed by $H_2O$ wash 15 ml for 5 min, 5 times. Films were then air dried overnight in a fume hood.

(d) Film Characterisation
(i) Acidic hydrolysis and Schiff Base Measurement

About 5 mg film and 1 ml 6N HCl was added in a screw-cap 1.5 ml polypropylene micro-tube and tightly sealed. The acidic hydrolysis was carried out in a heat block at 110° C. for 24 hours. After vortex-mixing, the hydrolysate solution was diluted 10 times with $dH_2O$ and then was scanned over the whole UV range by a UV-Vis spectrometer, the absorbance at 265 nm being specifically measured as the Schiff base concentration. Each film sample was analysed at least in triplicate, with a blank control. The results were expressed as the mean with standard deviation of triplicate values after subtracting the blank.

(ii) Equilibrium Swelling

About 15 mg cross-linked film was swollen by in 50 ml $dH_2O$ without agitation. The weight increase was measured after blotting the surface water with tissue. Most of the swelling of film reaches equilibrium in 24 h, while in the case of un-crosslinked films gradually dissolved in 30 min. The swelling ratio was calculated as: $E=(W_e-W_0)/W_0 \times 100$.

The results were expressed as the mean value and standard deviation for triplicate trials.

(iii) $\epsilon$-$NH_2$ Content Determination by TNBS Method

The primary amine group content (lysine residues) of fibrinogen films was determined using 2,4,6-trinitrobenzenesulfonic acid (TNBS) by a method modified from literature. To a weighed fibrinogen film sample (about 3 mg), 1.0 ml of a 4% $NaHCO_3$ solution (pH9.0) was added in a 20 ml Pyrex glass tubes with a crewed up cap (PTFE/rubber insert). After 10 min swelling at 40° C. in a water bath, 1.0 ml of a freshly prepared 0.5% TNBS solution (w/v) in distilled water was added. After reacting for 4 hours at 40° C., 3.0 ml of 12N HCl was added and the temperature was raised to 110° C. Solubilisation of fibrinogen was achieved within 1 hour, but the digestion was continued for 15 hours. The resulting solution was diluted with 5.0 ml $dH_2O$. The hydrolysate solution was then extracted with three 20 ml portions of anhydrous ethyl ether to remove excess unreacted TNBS and TNP-$\alpha$-amino group products. Every extract was processed by vortexing for 1 min and standing for 15 min to allow for phase separation. A 200 µl aliquot from the aqueous phase was put in the fume hood for 20 min to evaporate residual ether and diluted with 600 µl of $H_2O$. The absorbance was measured at 346 nm by the UV-Vis spectrometer. A control was prepared applying the same procedure with blank protein material. Every sample was processed by four replicates and absorbance readings were expressed after subtraction of the blank. The amine group content was calculated by:

$$\text{Moles Lys/moles protein} = 2 \text{ (Abs)} \times (0.02 \text{ l}) \times Mw / (1.46 \times 10^4 \text{ l/mole·cm}) \times 1 \text{ cm} \times x$$

Where Mw is the protein molecular weight with the unit of g/mole (340 k for fibrinogen); $1.46 \times 10^4$ l/mole·cm is the molar absorptive of TNP-lys; x is the sample weight in g.

Also, the relative amino group ratio was expressed as:

$$R_{NH2} = (\text{Mole Lys/moles modified Fbg})/(\text{moles Lys/Mole Fbg}) \times 100$$

(iv) Trypsin Degradation

The degradation of fibrinogen samples was performed using dilutions of standard 25 mg/ml in PBS Trypsin from bovine pancreas. The digestion was carried out in PBS saline pH 7.6, about 5 mg fibrinogen per ml enzyme solution in 37° C. incubator. Three enzyme: protein ratios were used, 1:100, 1:50, 1:20. The degradation process was monitored by measuring the protein concentration in the supernatant by standard BCA assay (Pierce, microplate method). At each 24 hr time point, 25 μl aliquots (in duplicate) were removed from each sample to quantify protein digestion, and the samples were replenished with 50 μl of fresh enzyme (same concentration) keeping the volume constant. The enzyme digestion was carried out over 2 weeks. The results were expressed as the degradation ratio, which is calculated as:

$$(Wp_{protein\ in\ supernatant})/(Wp_{protein\ in\ total}) \times 100$$

The method follows the product protocol. For BCA calibration, fibrinogen instead of BSA was used as the standard. 25 μl protein solution was mixed with 200 μl BCA working solution. After incubation at 37° C. for 30 min, absorbance at 540 nm was read by microplate reader and protein concentration was calculated from the standard curve. The working range is from 20-2000 μg/ml.

(v) Denaturation Temperature Measurement by DSC

The effect of cross-linking on the hydrothermal denaturation phenomena of fibrinogen film was observed by differential scanning calorimetry (DSC) (TA, 1000). The equipment was calibrated with Indiulium and Gallium. 3 mg equilibrium hydrated film was sealed in an aluminium pan, with an empty pan as reference. The heating rate of 5° C./min was used and a temperature interval between 30 and 100° C. was chosen. The peak temperature was recorded as the denaturation temperature.

(vi) ATR/FT-IR Scanning Spectrum

The chemistry component changes of the film were observed applying a Shimadzu FTIR 8400 s by the attenuation of total reflectance mode. The scan range was from 4000 to 600 $cm^{-1}$, with a scan number of 64 and resolution of 4 [$cm^{-1}$]. The data was edited by Origin software.

(e) Fibrinogen Cross-Linking

Before cross-linking, fibrinogen film is opaque white in appearance, and with glutaraldehyde cross-linking its changes colour, ranging between pale yellow and light orange. The colour change increases with the concentration of glutaraldehyde applied, up to 1%, but remained the same at higher glutaraldehyde. By contrast, collagenous material such as bovine skin powder or gelatin turns to a yellow to brown (rather than orange) colour over the same range of glutaraldehyde concentration. The difference in colour range may be due to the relatively high aromatic composition of fibrinogen in comparison with gelatin, supposing that these residues also react with glutaraldehyde in addition to lysine. $NaBH_4$ reduction significantly reduces the fibrinogen film colour, from white to light orange, and even paler for gelatin film. As a general observation, fibrinogen showed superior mechanical strength than gelatin.

TABLE 2

Weight of GTA cross-linked fibrinogen film

Fibrinogen

| GTA Con/% | GTA:protein (w/w/%) | Weight/mg | STDEV* | Weight increase/mg | Weight increase/% | Reduced film weight |
|---|---|---|---|---|---|---|
| 0 | 0 | 26.0 | ±0 | 0 | 0 | |
| 0.05 | 4 | 26.4 | ±1.0 | 0.4 | 1.5 | 28.3 |
| 0.1 | 8 | 29.7 | ±1.0 | 3.7 | 14.2 | 29.9 |
| 0.2 | 15 | 30.2 | ±0.9 | 4.2 | 16.1 | 29.9 |
| 0.4 | 31 | 30.5 | ±0.6 | 4.5 | 17.3 | 32.2 |
| 0.8 | 62 | 33.1 | ±2.0 | 7.1 | 27.3 | 32.2 |
| 1 | 77 | 31.9 | ±0.9 | 5.9 | 22.7 | 31.3 |
| 3 | 231 | 31.6 | ±0.3 | 5.6 | 21.5 | 31.2 |
| 5 | 385 | 30.8 | ±1.2 | 4.8 | 18.4 | 31.2 |

*based on three independent experiments

TABLE 3

Weight of GTA cross-linked gelatin film

Gelatin

| GTA Con/% | GTA/protein (w/w/%) | Weight/mg | STDEV* | Weight increase/mg | Weight increase/% | Reduced film weight |
|---|---|---|---|---|---|---|
| 0 | 0 | 40 | 0 | 0 | 0 | |
| 0.05 | 2.5 | 38.4 | ±0.2 | −1.7 | −4.3 | 40 |
| 0.1 | 5 | 40.6 | ±1.1 | 0.6 | 1.5 | 41.5 |
| 0.2 | 10 | 40.7 | ±1.6 | 0.7 | 1.8 | 42.2 |
| 0.4 | 20 | 41.7 | ±0.9 | 1.7 | 4.2 | 43.1 |
| 0.8 | 40 | 41.8 | ±0.4 | 1.8 | 4.5 | 41.1 |
| 1 | 50 | 42.3 | ±0.3 | 2.3 | 5.8 | 40.4 |
| 3 | 150 | 42.5 | ±0.3 | 2.5 | 6.2 | 41.2 |
| 5 | 250 | 41.6 | ±1.9 | 1.6 | 4 | 41.9 |

*based on two independent experiments

The relationship of GTA concentration used to mass gained is biphasic, with increasing mass up to an optimum GTA value (0.8% for Fbg, 3% for gelatin). Beyond this, there is progressively less mass increase so that, even with a large w/w excess of GTA (e.g. 5% GTA was 3.85 times the mass of Fbg). This weight gain reflects to some extent how much GTA is incorporated into the protein polymer; however, there is also some loss of protein material into crosslink buffer and by thorough washing (which has been observed with BCA reagent colouration). Hence the net mass is the resultant effect of two opposing factors: GTA incorporation and protein release. The protein loss from leaching is expected to be greater with low cross-linking, and also at very high GTA concentrations, due to increased mono-point modification rather than crosslinking and stabilization the molecule. Comparison of the Fbg and gelatin data shows differences in behaviour. At the same GTA concentration, Fbg shows greater proportionate weight gain than gelatin, and the maximum proportional gain of Fbg is over 4 times that of gelatin. The main reason may be a relative abundance of reactive residues (FIG. 14) but Fbg may form more intermolecular cross-links at the protein molecular surface than gelatin (because of intramolecular steric hindrance). Treatment of GTA films with $NaBH_4$ reduction has very little effect on the film weight, indicating that it does not cause a gross disruption of the cross-linked protein structure.

(f) Schiff Base Measurements

Figure 15:
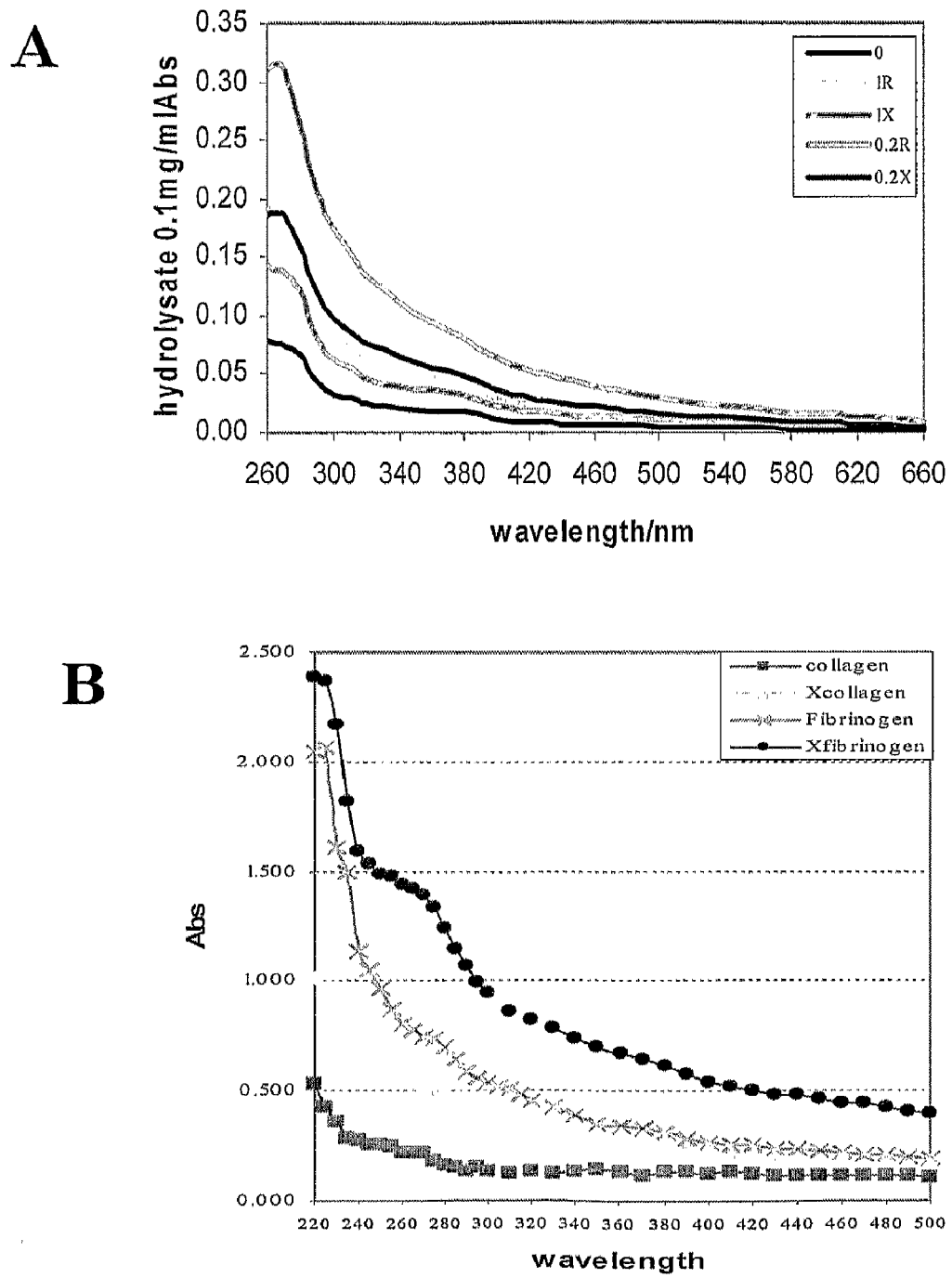
Figure 16:
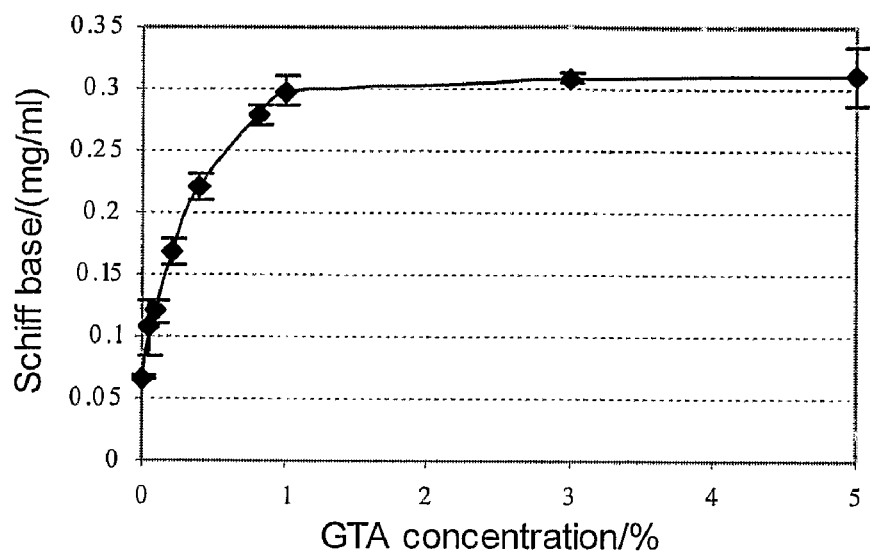
Figure 16:
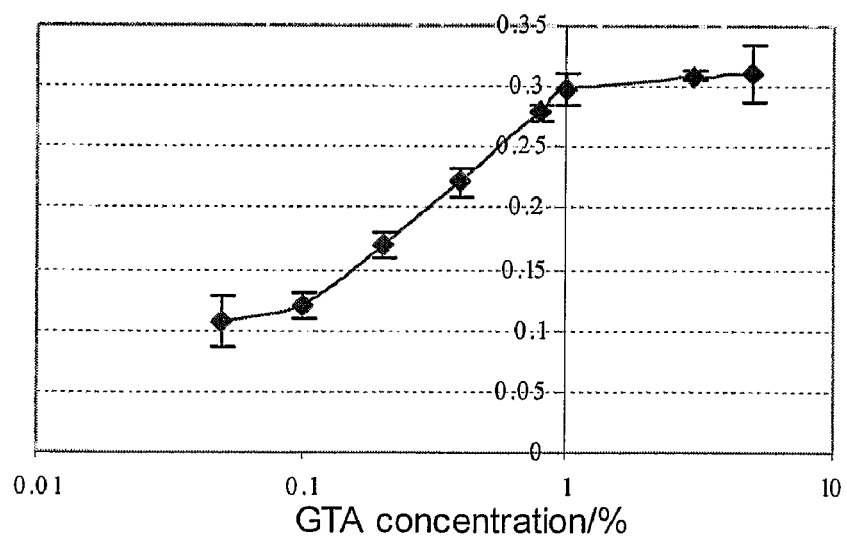

The acidic digestion liquid of GTA treated Fbg was a dark brown colour whose intensity depended on the GTA concentration. This was distinct from that of collagen or gelatin, which is light yellow. The characteristic Schiff base UV absorbance at 265 nm was observed with GTA treated Fbg Samples, and was also related to GTA concentration (FIG. 15). This was observed even though non-cross-linked Fbg hydrolysate has a relatively strong absorbance over the whole UV range, probably reflecting it's high proportion of aromatic amino acids (FIG. 15A). Even so, the absorbance after deduction of background absorbance of untreated Fbg samples could be considered a sensitive measure of Schiff base level and hence a GTA-crosslink density index in cross-linked fibrinogen. By comparison, the 265 nm peak also occurs in the spectrum of cross-linked collagen, and absorbance for untreated collagen is quite low (FIG. 15B). As it is correlated with the uptake of GTA, it could be considered a sensitive measure of Schiff base level and hence a GTA-crosslink density index in cross-linked fibrinogen. By comparison, the 265 nm peak also occurs in the spectrum of cross-linked collagen, and the absorbance for untreated collagen is relatively low (FIG. 15B). It is notable that the high background impairs an absolute measure of GTA incorporation into Fbg by this method. Also, to infer uptake by measuring free GTA residue remaining in the spent cross-linking liquid is error-prone, because leached protein from the film reacts with free GTA. The relationship between GTA uptake and the crosslink density is complex, because not all the aldehyde groups react with protein lysine residues. FIG. 15 also illustrates that $NaBH_4$ reducing treatment significantly reduced the absorbance (about 30%) and the film colour, effecting both the double bond and free aldehyde group, functioning to further stabilise the structure.

The Schiff base content of the Fbg films increases with the GTA concentration in an approximately exponential relationship (FIG. 16A), giving a sigmoidal curve on a log[GTA] scale (FIG. 16B) and a plateau above 1% GTA. This data broadly concurs with the previous data showing maximum weight increase 0.8% GTA. At 1% concentration, the mass ratio of GTA to Fbg is 0.769, the equivalent molar ratio being 6579, gives an estimate of the maximum cross-linking density to be on average as many as 23 molecules of GTA (GTA polymer) per lysine residue (284 lys/Fbg molecule). However, in reality some Lys residues may be sterically protected from GTA. If we suppose average of polymerization degree of GTA as 5, at 0.05% GTA condition the reacted lysine could be 20% of total, as seen from Table 4.

TABLE 4

Theoretical calculation of GTA:Fbg ratio and reacted lysine ratio.

| | GTA Con/% | | | | | | | |
|---|---|---|---|---|---|---|---|---|
| | 0.05 | 0.1 | 0.2 | 0.4 | 0.8 | 1 | 3 | 5 |
| GTA/Fbg (w/w) | 0.038 | 0.077 | 0.154 | 0.308 | 0.615 | 0.769 | 2.207 | 3.845 |
| GTA/Fbg (Mole/Mole) | 329 | 658 | 1316 | 2632 | 5263 | 6579 | — | — |
| GTA/Lys (Mole/Mole) | 1 | 2 | 5 | 10 | 19 | 23 | — | — |
| Reacted Lys ratio | 20% | 40% | 100% | — | — | — | — | — |

(g) Equilibrium Swelling Ratio

Equilibrium swelling ratio is not only a measure of the degree of cross-linking but also an indicator of the biomaterial's mechanical stability in the hydrated (physiological) state. The decrease of swelling ratio for the polymers is usually due to two consequences of cross-linking: first, the linkages introduced into the polymer molecule by inter or intra molecular type to form molecular aggregation and supramolecular network; second, the reactions may involve conversion of a polar residue (e.g. Lysine) to a less polar adduct (e.g. GTA-Schiff-base), thereby giving a net loss of hydrophilic groups, and addition of hydrophobic character from the cross-linker (e.g. in the case of GTA, additional hydrophobicity is imparted by the polymerized and conjugated di-diene cross-link 'backbone').

The cross-linking GTA concentration effected the swelling ratio of the resultant Fbg films in an approximately exponential decay type relationship (FIG. 17), which reaches a low swelling ratio plateau of 47% above 1% GTA. Between 0.05% and 1%, the swelling ratio rapidly drops with increase of the cross-linker's concentration, for instance at 0.05% GTA the film has gained a significant stability as swelling about 90%. By contrast, untreated Fbg film quickly dissolves in water. This relationship broadly concurs with the Schiff-base data (Example 10(f)); however, the swelling ratio rises very slightly from 1-5% GTA, which may be due to increased mono-point GTA reactions, as suggested by the biphasic weigh change data. Change in hydrophobicity has not been measured but cross-linked films show a relatively hydrophobic surface wetability.

(h) $\epsilon$-NH2 Content

Figure 18:
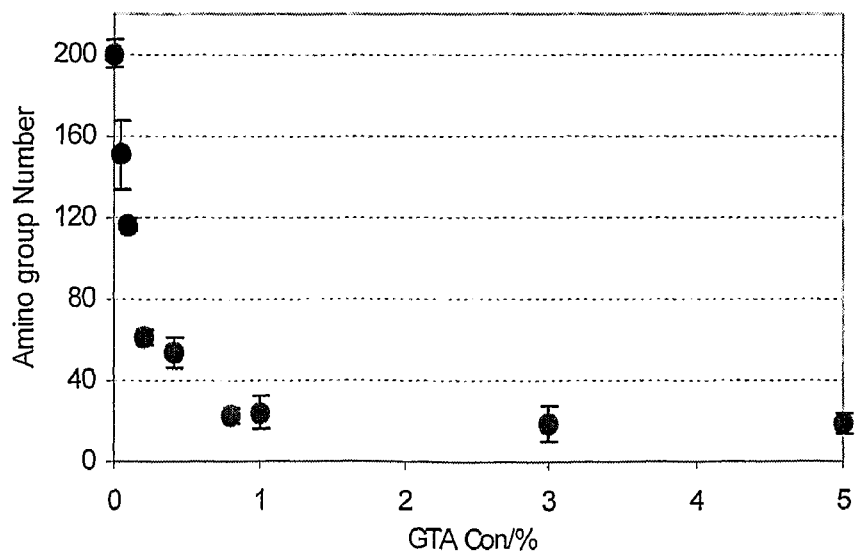

This investigation demonstrated a loss of free $\epsilon$-amine in Fbg films dependent on the GTA cross-linking concentration. The relationship, over the range studied, concurs with the measurements of Schiff base density and equilibrium swelling (FIG. 18). The critical GTA concentration for maximal reaction with lysine is between 0.8%-1%, when the lysine conversion achieved to 90%, above which there is a plateau of around 10% non-reacted lysine. Significant loss of free $\epsilon$-amine occurs at very low GTA concentration. Even at 0.05%, the lowest concentrated studied, 20% lysine reacted, and at 0.1% GTA, there is a 40% loss. These data accord with the prediction in Table 4 derived from the Schiff-base measurements.

(i) Trypsin Degradation

Figure 17:
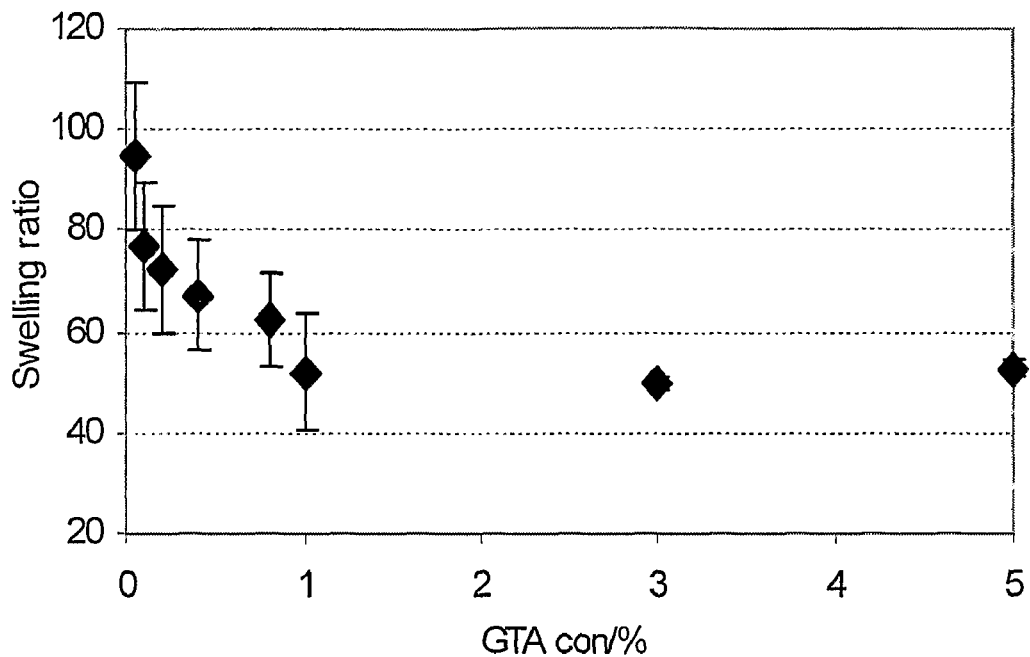
Figure 19:
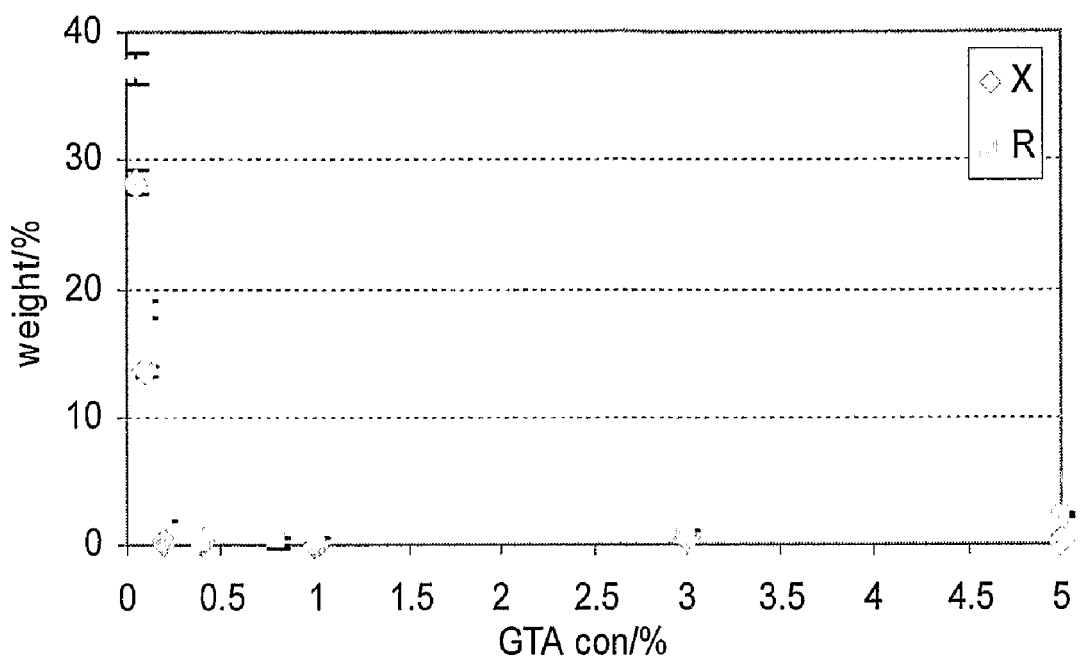

The trypsin degradation of Fbg films with different GTA concentration is shown in FIG. 19. The conditions were: trypsin concentration 0.25 mg/ml in PBS buffer pH7.6, Enzyme: Fbg film 1:20 (w/w), 24 hour digestion at 37° C., and soluble peptide was measured by the BCA method. The least cross-linked film (0.05% GTA) almost completely dissolved by 24 hr giving yellow coloured turbid digestion liquor. The soluble peptide degradation products were found to be 28% of the total mass. The 0.1% GTA sample was partially dissolved with 14% weight loss recovered in solution; the 0.2% GTA treated film was seen swollen and lost 2% weight. The films treated by higher GTA concentration (0.8% to 1%) were relatively stable, retaining their shape, and almost no weight loss, with the soaking solution keeping clear. However, for 3% and 5% GTA samples a small amount of protein leaching was detected with 0.5% weight loss, consistent with the equilibrium swelling result (FIG. 17).

These data indicate that 1% GTA gives greatest Fbg stabilisation, with more GTA giving slightly less stability. Although shown at 24 hr, with longer incubations, over several days, results in more degradation of 3 and 5% crosslinked matrices. Trypsin cleavage sites on the protein substrate are at basic amino acid residues such as lysine, which are the sites of GTA reaction. It would therefore be expected that trypsin resistance would follow the number of free lysine residues in the crosslinked protein. The primary epsilon amino group determination shows a similar but slightly decreasing, for 1%, for 3% and 5% GTA, would predict that resistance to trypsin should gradually increase over the same range. Three factors could be proposed to contribute to cross-linking related resistance to enzymatic proteolysis: first, crosslink modification causes loss of enzyme recognition and cleavage sites; second, cross-linking causes steric hindrance by shielding and blocking enzyme access to specific cleavage sites, third, the proportion of monopoint compared to cross-linked reaction of the cross-linking reagent. The results suggest that increasing GTA concentrations above 1% causes a slight change in the reaction mode of GTA with protein, to an increase in monopoint modification, involving similar proportions of reacted lysine residues but less hindrance for enzyme attack. Below 1%, multipoint intramolecular cross-linking is the dominant reaction mode but for 0.05%-0.1%, intermolecular cross-linking is believed to predominate. Furthermore, as seen from FIG. 19, the enzyme degradation stability of the fibrinogen material can be controlled by adjusting the cross-linking density over the range of 0.05%-1% GTA.

FIG. 19 also illustrates that the effect of NaBH$_4$ reduction is to increase the amount of trypsin degradation by nearly 50%, at every GTA concentration. This could be explained by the effect of reduction on the polymeric GTA cross-link structures if free aldehyde group and conjugated Schiff base and polymerized $\alpha,\beta$ unsaturated di-diene are more resistant to enzyme digestion than saturated structure in reduced films.

(j) Thermal Denaturation Temperature Determination by Differential Scanning Calorimetry Differential scanning calorimetry (DSC) has proved to be a useful and powerful approach to characterize temperature induced conformation changes of biological macromolecules. For collagen material, cross-linking causes a high-shift of denaturation temperature ($T_d$) relating to the degree of cross-linking and concurs with primary amine content and enzyme degradation stability determination. Untreated bovine skin collagen has $T_d$ of 64° C., and maximal GTA crosslinking can raise the $T_d$ to 85° C. This denaturation transition is irreversible and endothermic, due to collagen molecule triple helix deformation or "melt".

Figure 20:
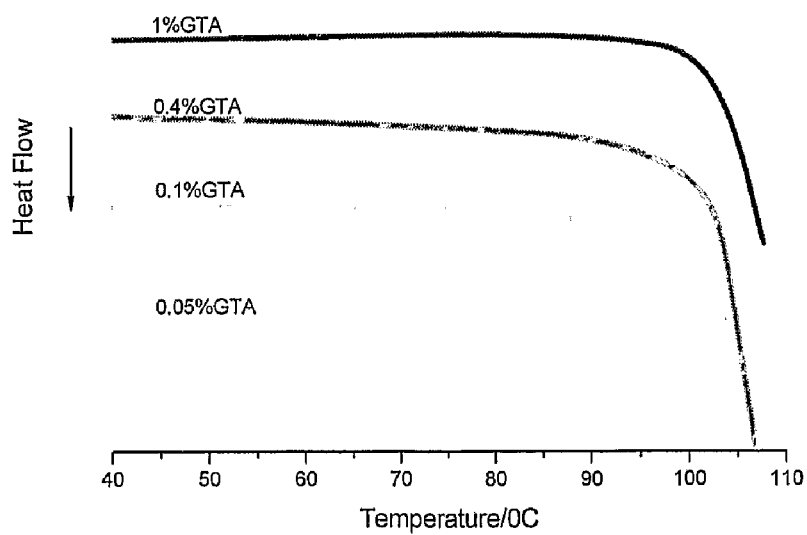

The thermal conformational changes of fibrinogen by DSC have also been investigated by some researchers to study the protein structure, but not cross-linking effects. In contrast to collagen, fibrinogen shows two distinct stages of denaturation, a 61° C. endothermic peak from the D domain and 100° C. peak from the E domain. A weak and wide transition at 78° C. was also reported as attributed to the C-terminal parts of A$\alpha$ chains of Fbg. The DSC spectrum obtained from Fbg films cross-linked over a range of GTA is shown in FIG. 20. Only very low cross-linked Fbg (0.05%) shows a clear, characteristic transition peak. The 61° C. peak is almost absent but other two remain. This curve suggests that at low GTA concentration it reacts more with two D domains rather than the central E domain. However, the small increase from 0.05% to 0.1% or 0.4% GTA causes both of high temperature peaks to almost disappear as well, leaving partially unstable slopes. With 1% GTA, the curve is even flatter with a very weak and wide endothermic area corresponding to E domain denaturation, which indicates more stability or rigidity of the whole Fbg structure introduced by GTA cross-linking. Unlike collagen, these results do not show a progressive relationship between GTA concentration and denaturation peak shift, but do suggest some preferential susceptibility of the D domains for GTA.

(k) Optimisation of Fibrinogen Crosslinking by Glutaraldehyde (i) Proportion of GTA Investigations have found that the amount of GTA is more important than concentration itself, and therefore the volume of reaction solution should be determined in practice. In the results and discussion above, the GTA concentration achieving greatest stabilisation in the model is 1%, when 2 ml of crosslinking buffer is applied to 26 mg Fbg, giving a ratio of GTA: Fbg is 0.77:1 (w/w) or 6579:1 (molar:molar).

Figure 21:
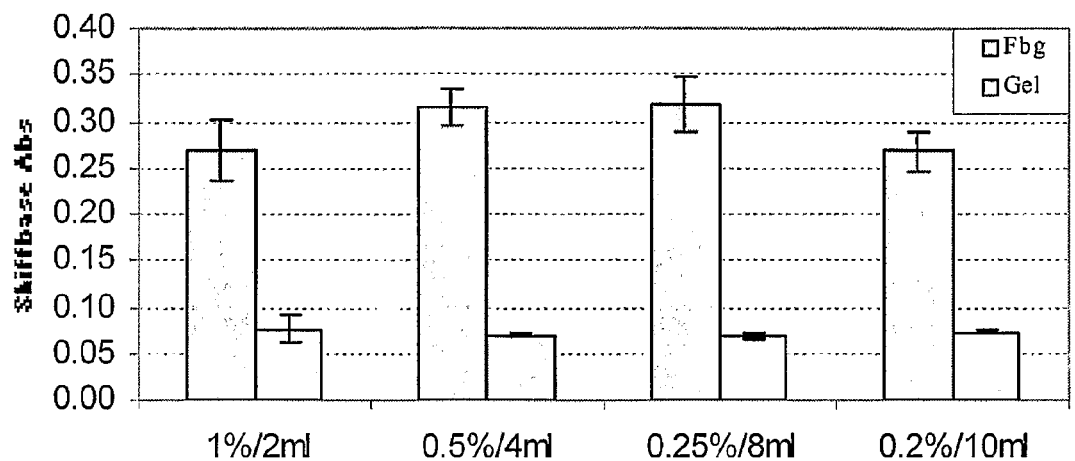

The effect of concentration used to apply the same amount ratios of GTA, on resultant Fbg crosslinking density, was evaluated (FIG. 21). Four applied concentrations (0.2%, 0.25%, 0.5%, 1%) gave slight variation in crosslinking densities for both Fbg and gelatin but of only minor significance. The results showed that 2 ml of 1% GTA gave similar crosslinking density as 10 ml of 0.2% GTA. The slightly higher cross-link density given by 0.25% or 0.5% GTA may due to more even penetration and reaction into the film matrix; the low reactant concentration of the 0.2% solution could have reduced uptake equilibrium by protein film from the reaction media. The small variations could therefore reflect some GTA concentration dependent kinetic effects, but the substantial similarity in cross-linking suggests that it is substantially complete over 24 hours.

(ii) Cross-Linking Reaction Time

Figure 22:
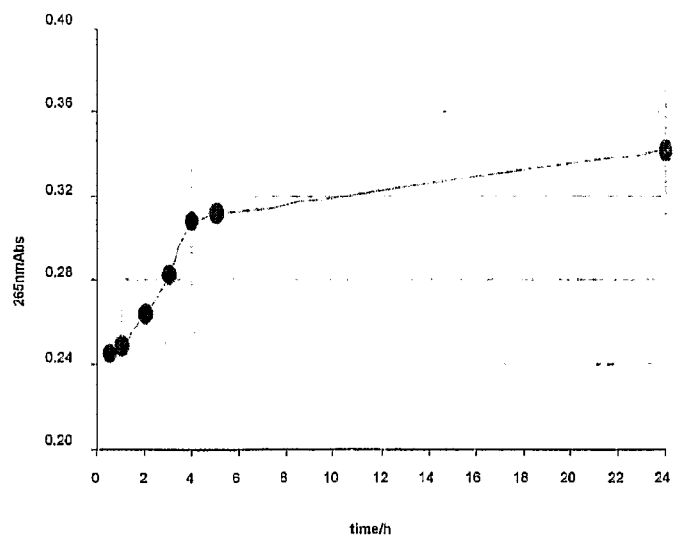

The cross-link density, characterised by Schiff base formation, was observed to increase with time, as shown in FIG. 22. The reaction reaches substantial completion at 4 hours with little further increase at 24 hours. This runs contrary to published observations for GTA-Collagen cross-linking monitored by increasing $T_d$, showing maximal reaction occurs between a few minutes to ½ hour at the RT and neutral pH in an aqueous medium. However, it should be noted that our study is performed in 80% ethanol aqueous buffer, and the organic solvent will certainly slow down the reaction.

(iii) Cross-Linking pH

Figure 23:
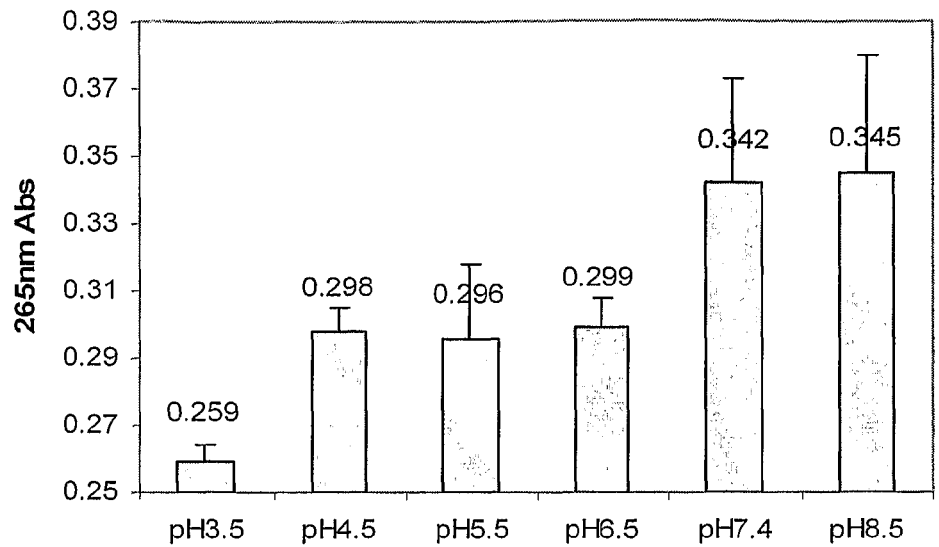
Figure 24:
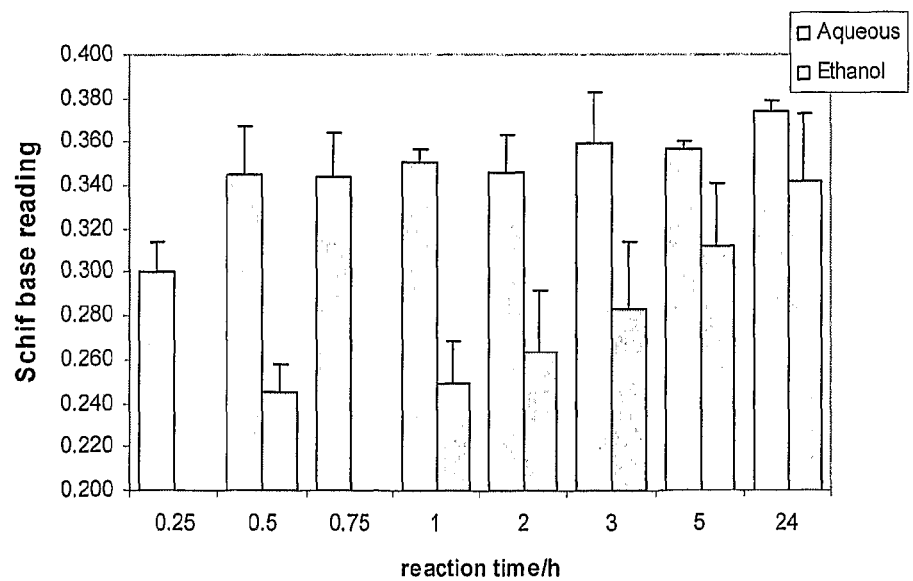

The effect of the reaction media pH on Schiff base formation is shown in FIG. 23. The films obtained at different pH showed a variation in the depth of yellow colour, darkening with rising pH. Correspondingly, the Schiff base concentration in acidic conditions (pH 3.5) is very low but substantially higher at pH 4.5. There was little increase between pH 4.5-pH 6.5, but a further increase at pH 7.4 to pH 8.5. The results concur with the structure and pH dependent reaction mechanism of GTA described hereinbefore. At neutral or slightly alkaline conditions, the conjugated Schiff base is the dominant product of the GTA-protein reaction, which is stable to acidic digestion. At low pH 3.5, this is a minor product, and other structures are not acid-stable. The lower cross-linking density at pH 4.5 to pH 6.5 may also reflect the pI of Fbg, which is around pH 5.5-5.8, which may influence the access of GTA.

(iv) Cross-Linking Media

Both aqueous and Ethanol/$H_2O$ (80:20 v/v) 0.1 M MES pH 7.4 buffer have been studied in the optimisation experiments described hereinbefore. The aqueous media gave higher cross-linking density and reaction rate than ethanolic media. As seen from FIG. 24, in aqueous medium the reaction reaches completion by ½ hour, and the crosslink density is about 1.4 times that of the ethanolic media. Although the reaction in the ethanolic buffer does reach completion by 24 hours, the total extent of reaction is slightly lower than in the $H_2O$ system.

Figure 25:
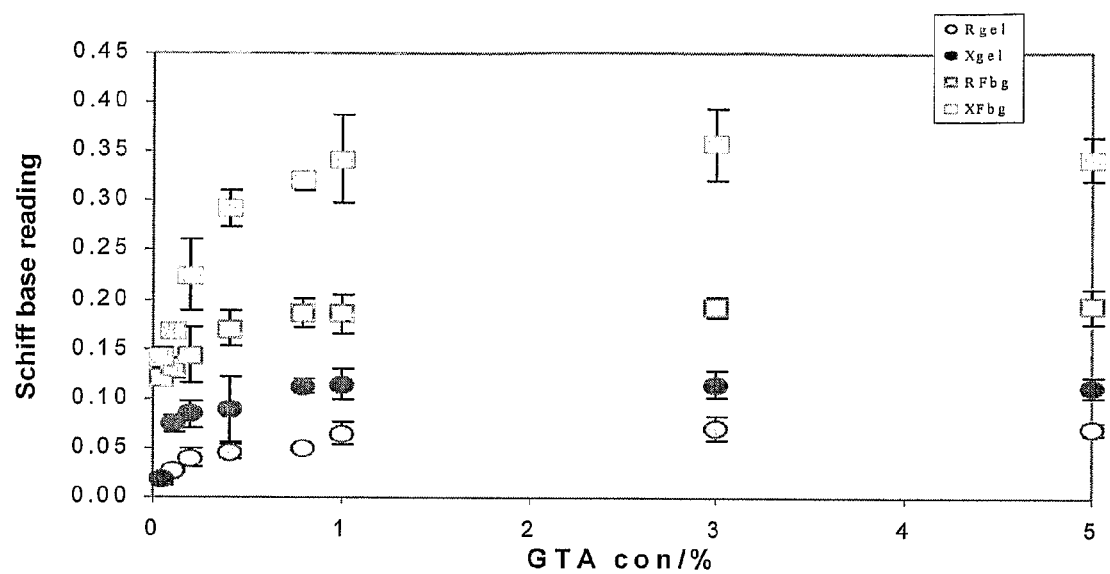

(I) Optimisation of Sodium Borohydride Reduction for Glutaraldehyde Cross-Linked Fibrinogen The reducing agent $NaBH_4$ reacts with both carbonyl and double bonds, thus converting the aldehyde groups and conjugated Schiff base to the saturated structures. The GTA crosslinking would benefit from this post treatment both by stabilising the structures and by quenching the reactive groups (detoxification). FIG. 25 shows the Schiff base determination for Fbg and gelatin crosslinked with different GTA concentrations and then reduced. The Schiff base level for Fbg is over twice that of gelatin, and the maximum level for both proteins are close to 1%. The reduced protein curves have a similar trend. For densely crosslinked Fbg, the reduction treatment depletes 50% Schiff base and for gelatin, only about 30%. At lower crosslinking (from 0.05%-1%), the depletion of Schiff base is proportionate to the GTA concentration for Fbg, but for gelatin it is constant. The results show that for both proteins, $NaBH_4$ treatment eliminates only up to 50% of detectable Schiff bases in the crosslinked protein. This suggests the remaining Schiff base structures may be sterically protected by the protein molecule, raising the question of whether further quenching can be achieved by enhanced reduction.

Figure 26:
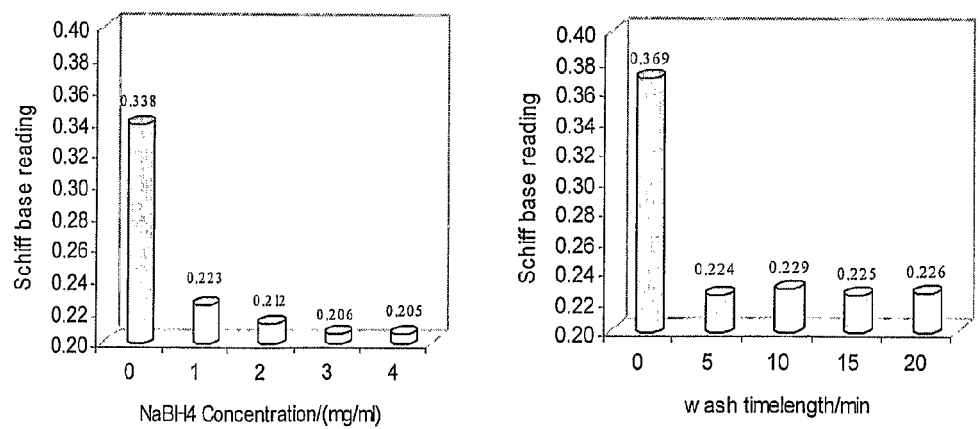

Different $NaBH_4$ concentrations, or reduction time length have been investigated in the study based on the optimal GTA crosslinked sample (GTA1%, Crosslinked 4 hours, pH 7.4, RT). The results are shown in FIG. 26. For 15 ml×5 min×5 reduction washes, 1 mg/ml $NaBH_4$ effectively cut the Schiff base reading while double $NaBH_4$ concentration to 2 mg/ml only slightly further decrease the Schiff base reading; raising the concentration 3 or 4 folds still keep at the same level. Longer wash times, also attempted, fail to achieve further reduction on Schiff base, and shows that the achievable reaction is finished in 5 minutes.

The mechanical strength of cross-linked protein films was observed to weaken during the reduction procedure. As noted in Example 10 (i) the enzyme degradation stability also slightly decreases when compared to the unreduced counterparts. An affect on protein structure is also evidenced by DSC results (FIG. 27) and FT-IR (FIG. 28).

Figure 27:
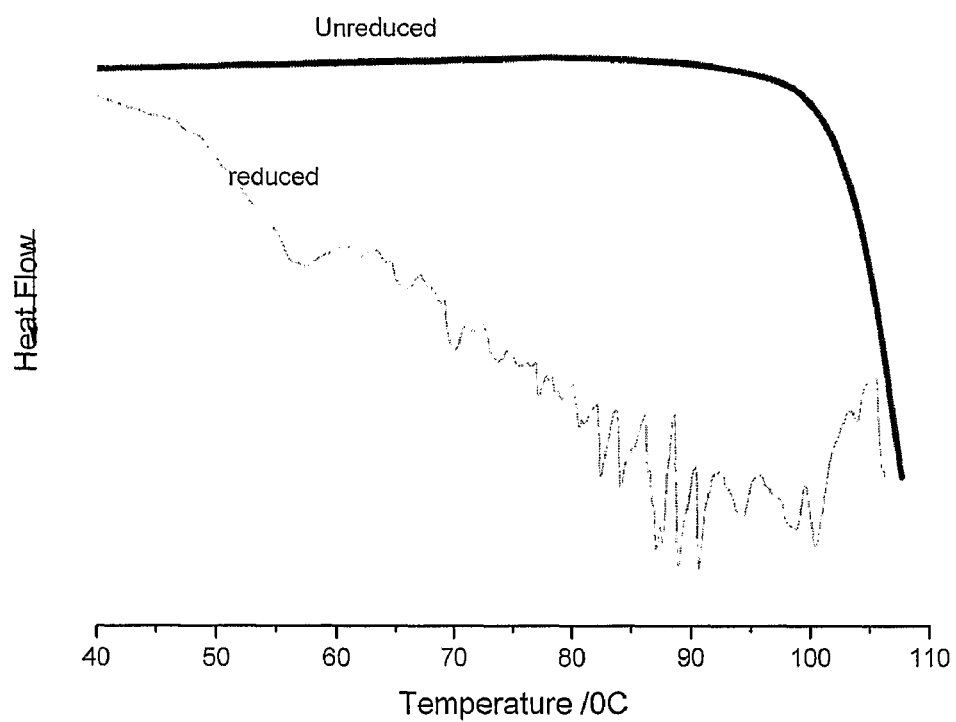

As seen from FIG. 27, the hydrothermal stability brought by GTA 1% crosslinking to Fbg conformation is largely abolished by 1 mg/ml $NaBH_4$ reduction. The 55° C. peak which is attributed to the Fbg D domain transition has reappeared; furthermore, endothermic absorption returns until 100° C. This result is indicative of restoration of flexibility and mobility in the D domains, which could be due to conversion of the rigid alkene or conjugated Schiff based (C=C and C=N) structures to saturated and flexible alkane backbone (C—C and C—N).

Figure 28:
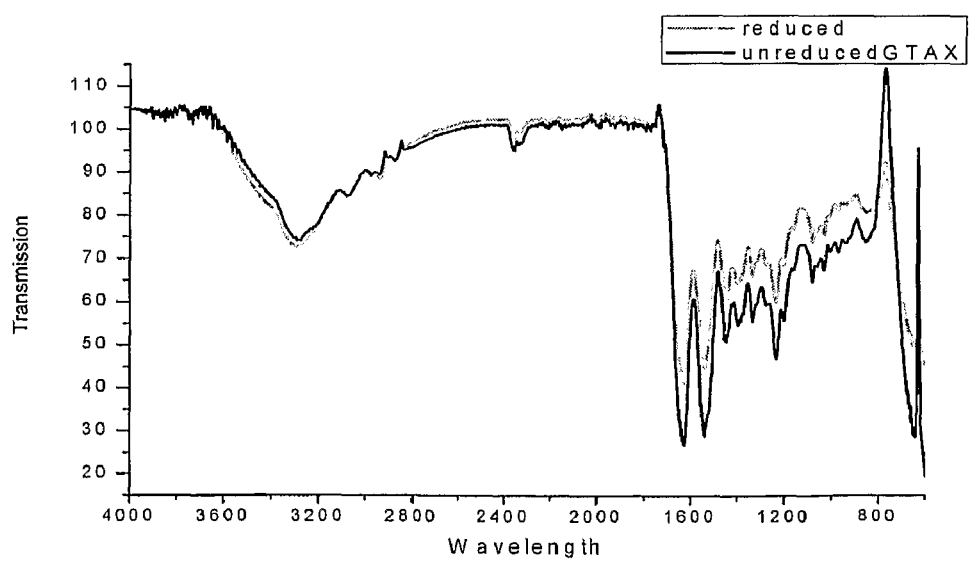

The Fourier Transform-Infrared (FT-IR) spectrum of reduced compared to unreduced film shows a weaker absorbance over the range 1655-800 cm$^{-1}$ (FIG. 28). The IR spectra of Schiff base features a band corresponding to a C=C bond at 1650-1655 cm$^{-1}$, and a band of the C=C bond in the 1610-1620 cm$^{-1}$ region. $NaBH_4$-reduction shows that both bands have been reduced. Reduction of the C=N bond with $NaBH_4$ has been proved to remove the imine adsorption band at 1650 using model compounds (amino acid-malonaldehyde). Although there is not a strong signal for aldehyde carbonyl group band at 1700 cm$^{-1}$ (maybe due to overlap to C=O or C=N), $NaBH_4$ has been employed as the primary reductant in organic synthesis for aldehydes to alcohol conversion. The 1655, 1546, 1458 cm$^{-1}$ peaks attributed to the band of amide (C=O carbonyl linked with N), typically exist in peptides. The spectra may also indicate there is possibility for reduction on peptide carbonyl. As more potent reduction probably damages the integrity of the primary protein structure and its material stability, 1 mg/ml or 2 mg/ml concentration is preferable.

Example 11

SEM Analysis of Fibrin/Alginate Scaffold

Figure 29:
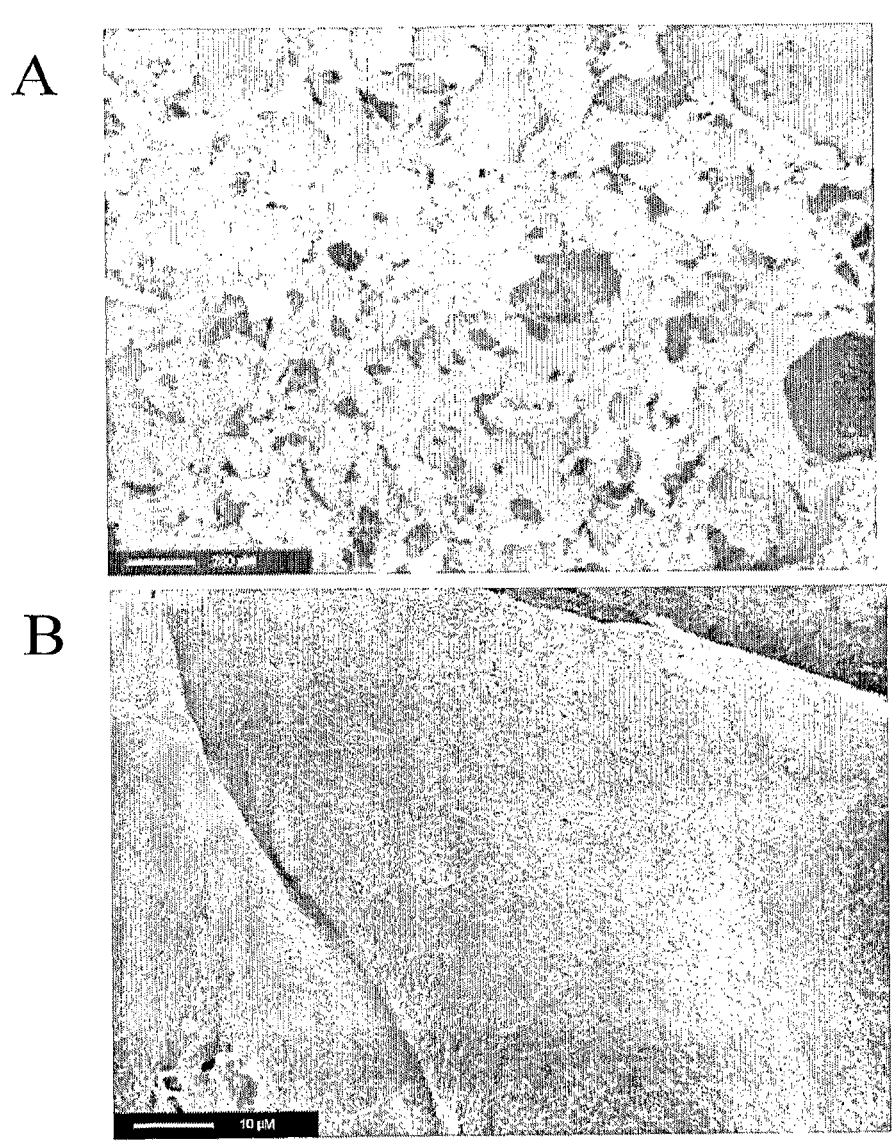

A composition comprising 1% Fbg/thrombin/1% alginate/50 mM $CaCl_2$ foam was cross-linked with 0.2% GTA in 80% EtOH/20% MES pH7.4 for 4 hours, washed 5 times, lyophilised, and prepared for SEM. A 0.5×1 cm block cut and mounted on lab tape as a backing. The material was gold splutter-coated under vacuum and examined by SEM. The results of the SEM are shown in FIG. 29 where a fine structure of the material was seen to consist of a lamellar matrix of densely packed randomly oriented filaments.

The structural results indicate that the manufacturing process has allowed fibrinogen to form a coagulated network of fibres and is stabilised by alginate during the cross-linking and reduction process with retention of suitable macroscale (100-200 nm) and microscale (1-10 µm) porosity. This illustrates the feasibility of the process for forming a tissue engineered scaffold.

Example 12

Cytotoxic Analysis of Scaffold Components

The MTS assay was used as described hereinbefore with certain modifications.

Firstly, two modalities were used, (i) acute cytotoxicity and (ii) effect on proliferation over 3 days.

On day −1, human dermal fibroblasts were seeded for (i) at high density ($5\times10^5$/well) and for (ii) at low density ($2.5\times10^4$/well).

On day 0, cultures were washed in PBS/g and exposed to the test agent diluted into PBS/g unless otherwise stated, for a test period (1-4 hr). Then the test agent was removed and culture medium replaced. For (i), cells were returned to maintenance medium (2% FBS/DMEM) followed by MTS/PMS reagent for two hours. For (ii), cells were returned to growth medium (10% FBS/DMEC) for three days. After this period, the growth medium was aspirated and replaced with maintenance medium (2% FBS/DMEM) followed by MTS/PMS reagent for two hours.

MTS colour change at 2 hours was measured as described hereinbefore.

Test agents were GTA and soaked scaffold supernatants (a), fibrinogen and fragment E Schiff base hydrolysate (b) and (c) and alginate (d).

(a) GTA and Scaffold Supernatants

Figure 30:
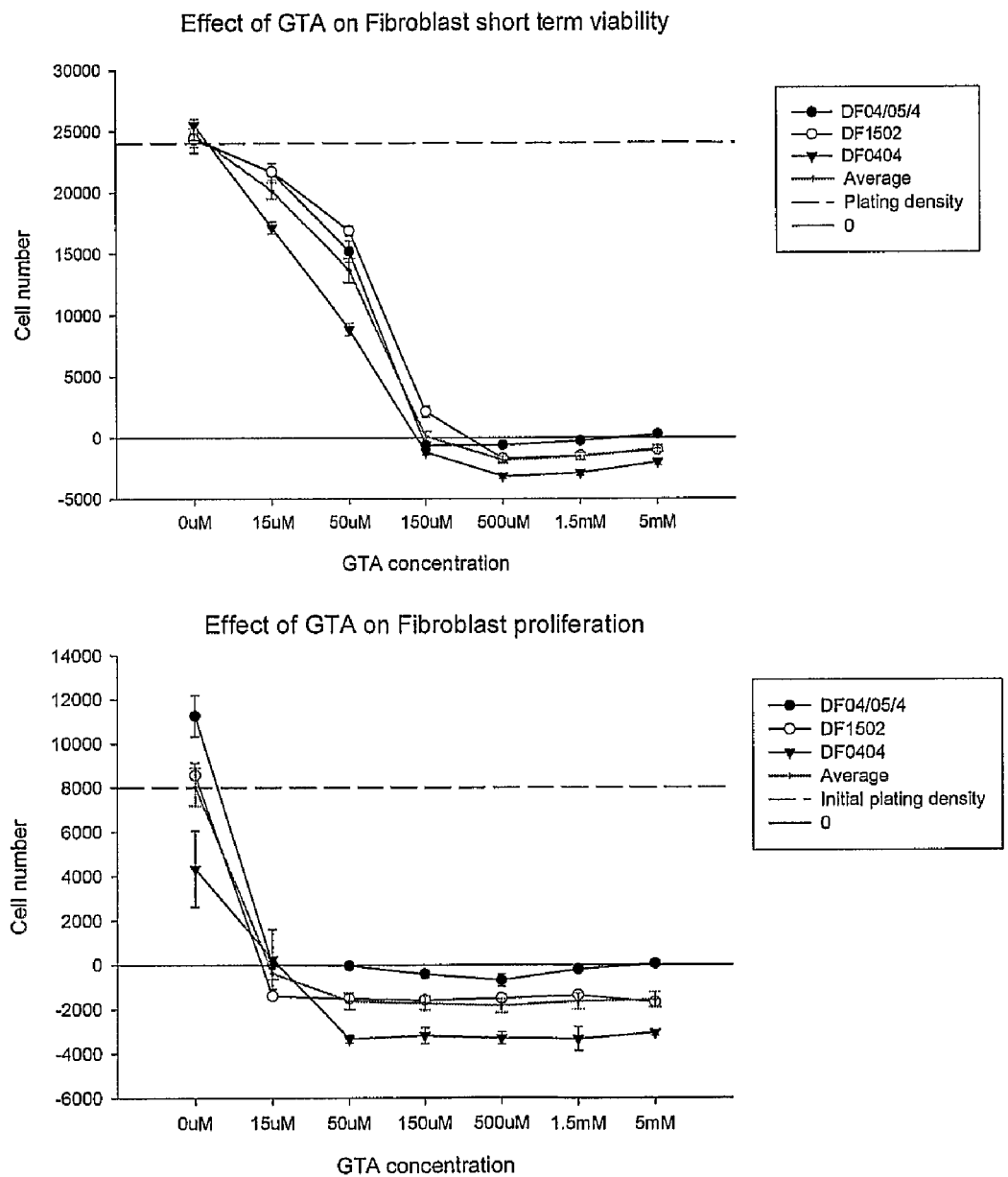
Figure 31:
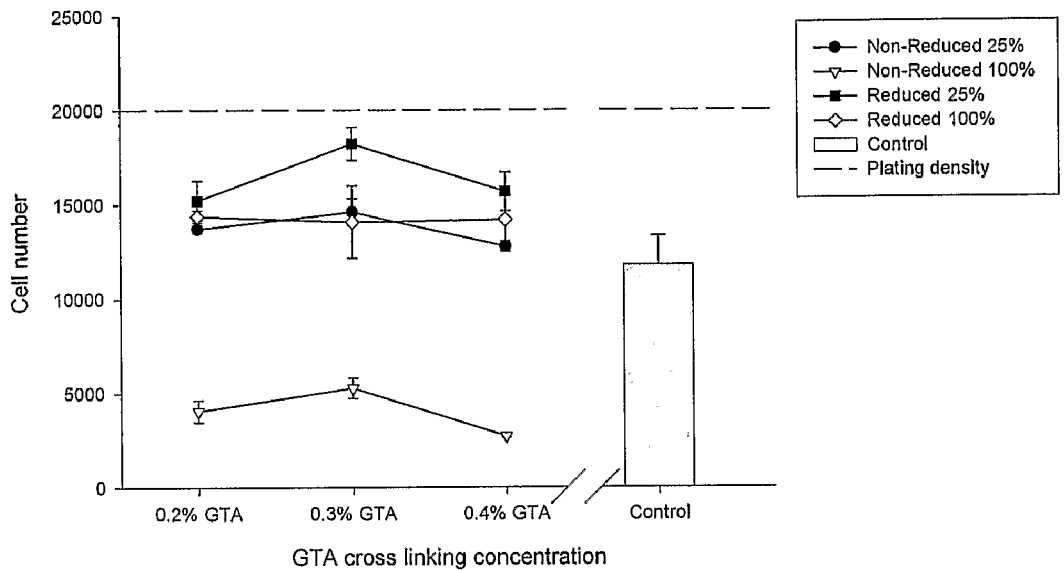
Figure 31:
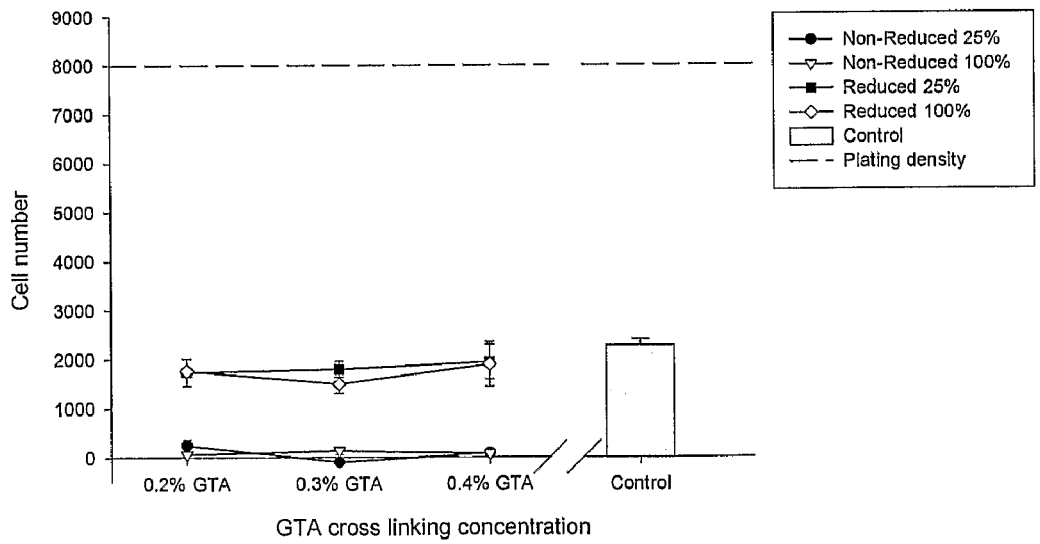

The results for GTA and Scaffold supernatants can be observed in FIGS. 30 and 31. The acute $LD_{50}$ for GTA on HDF cytotoxicity is around 50-150 μM, and for proliferation it is more potent, around 7 μM.

Exposure of cells to PBS supernatant from non-reduced scaffolds soaked for one hour in PBS results in substantial cytotoxicity for proliferation and a marked acute cytotoxicity. Both these effects are prevented by the reduction process. On the basis of the GTA LD50 values above and dilution of the supernatant, the GTA-equivalent in the supernatant of non-reduced scaffolds is around 20 μM.

(b) GTA-crosslinked fibrinogen Schiff Base Hydrolysate

Figure 32:
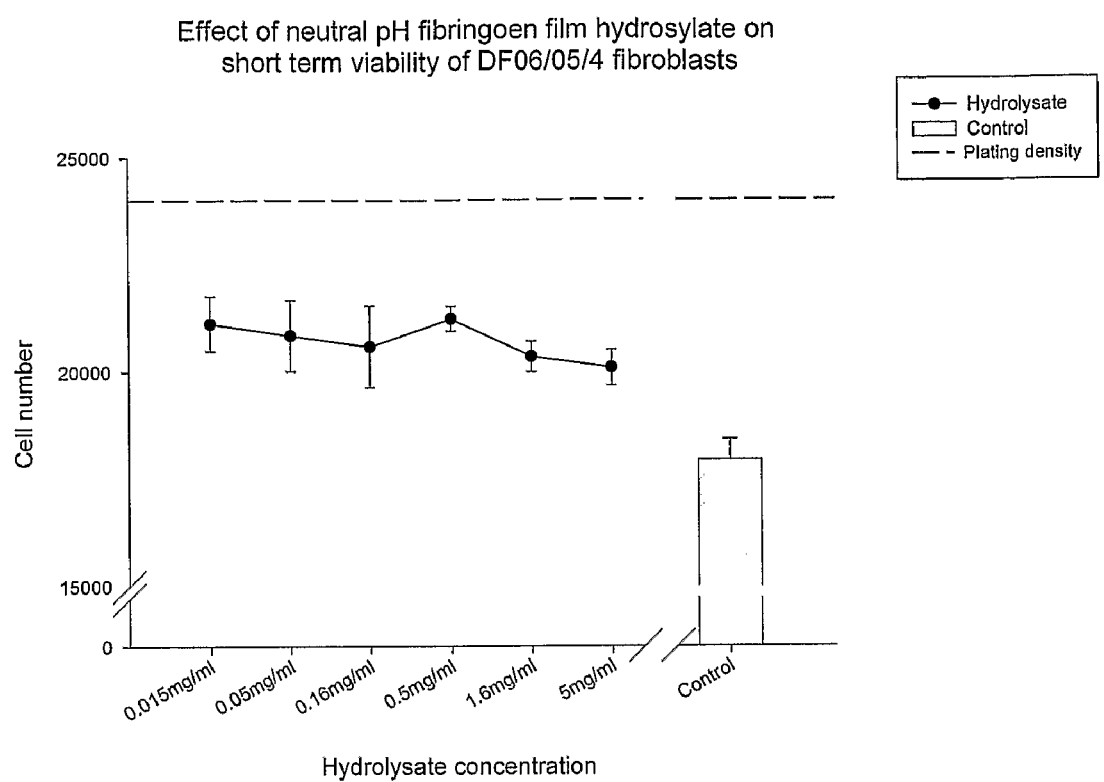
Figure 33:
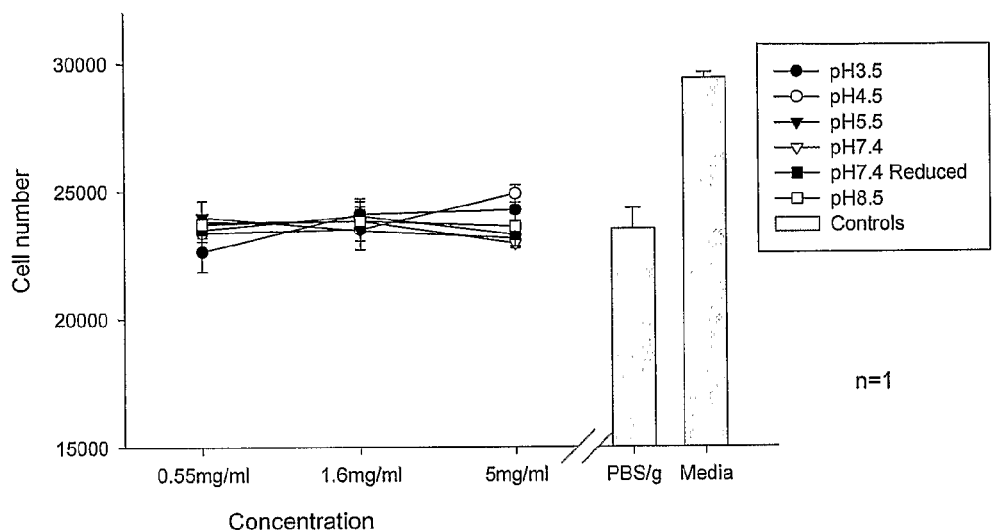
Figure 33:
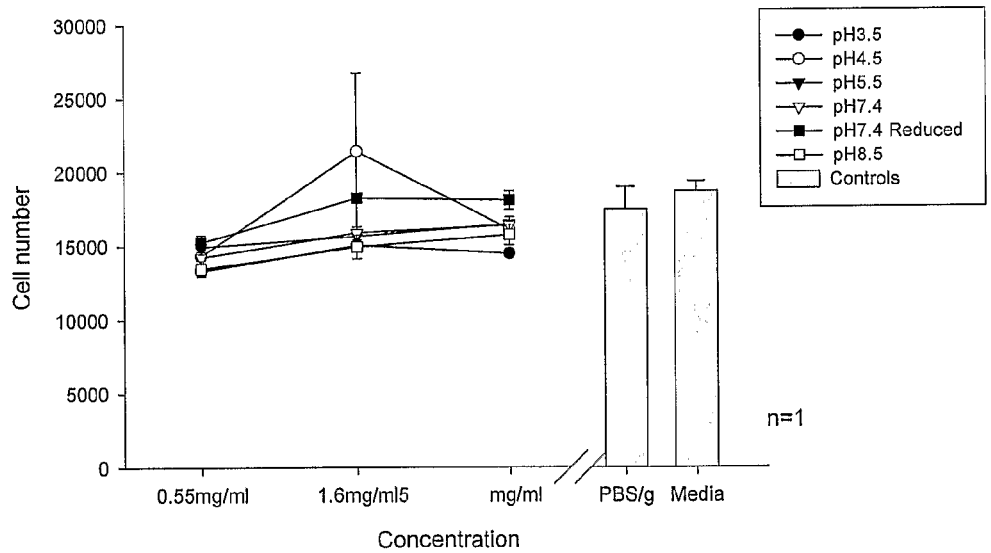

Schiff base hydrolysates were prepared as described hereinbefore and the results of this study can be seen in FIGS. 32 and 33. Some loss of cell viability due to incubating for 1 hr in PBS/g was observed compared to culture medium. However, no cytotoxic effects of Schiff base GTA-crosslinked fibrinogen hydrolysates were detected. These data provides evidence that the GTA cross-linked protein does not intrinsically cause cytotoxicity, contributing to the safe usage of GTA cross-linking.

(c) Fibrinogen Proteolytic Hydrolysates

Fibrin clots 10 mg/ml were lysed with trypsin or plasmin for 16 hours, and then further proteolytic activity was inhibited with soy bean trypsin inhibitor or aprotinin respectively, under conditions described hereinbefore. The equivalent fibrinogen protein in resulting hydrolysates was 7.5 mg/ml.

Figure 34:
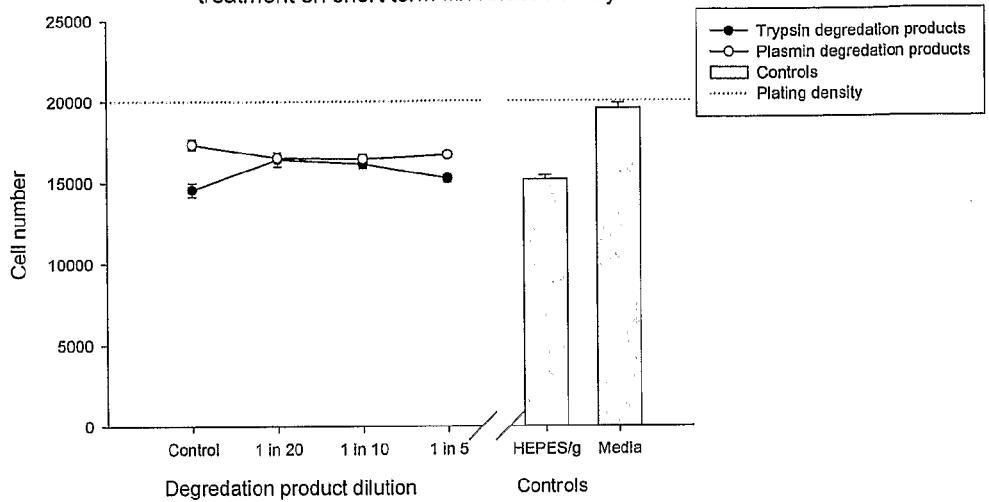
Figure 34:
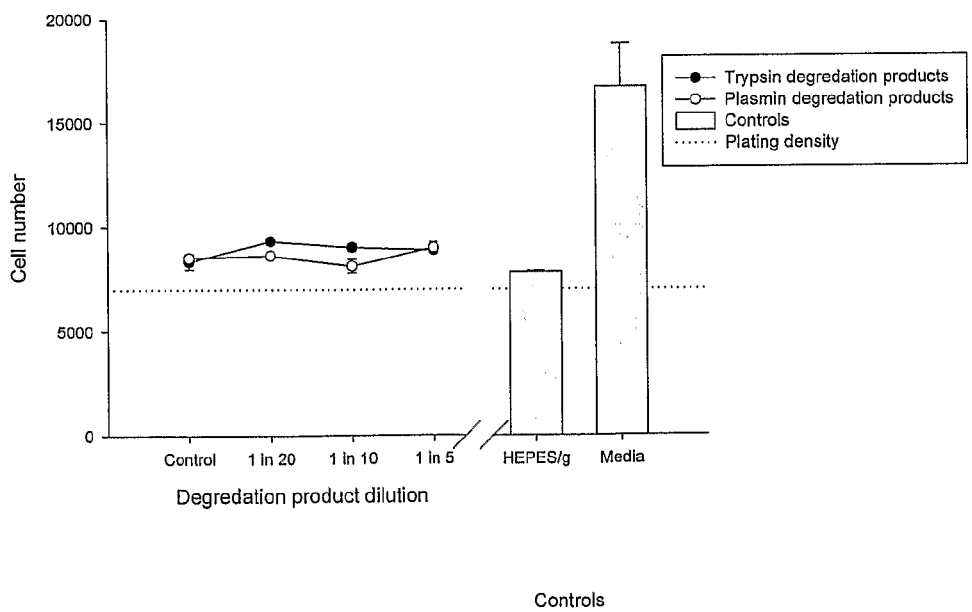

The results are shown in FIG. 34 where it can be seen that neither hydrolysate gave evidence of cytotoxicity suggesting that its natural proteolytic degradation is unlikely to cause adverse cytotoxicity. This data supports the safety use of fibrinogen as a scaffold material.

(d) Sodium Alginate

Figure 35:
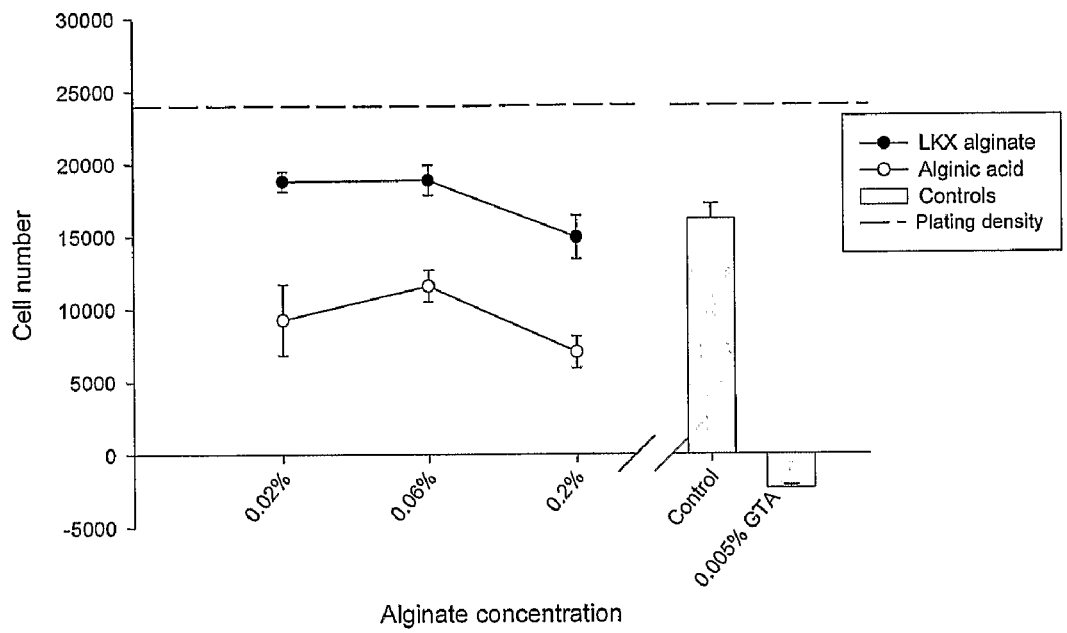
Figure 35:
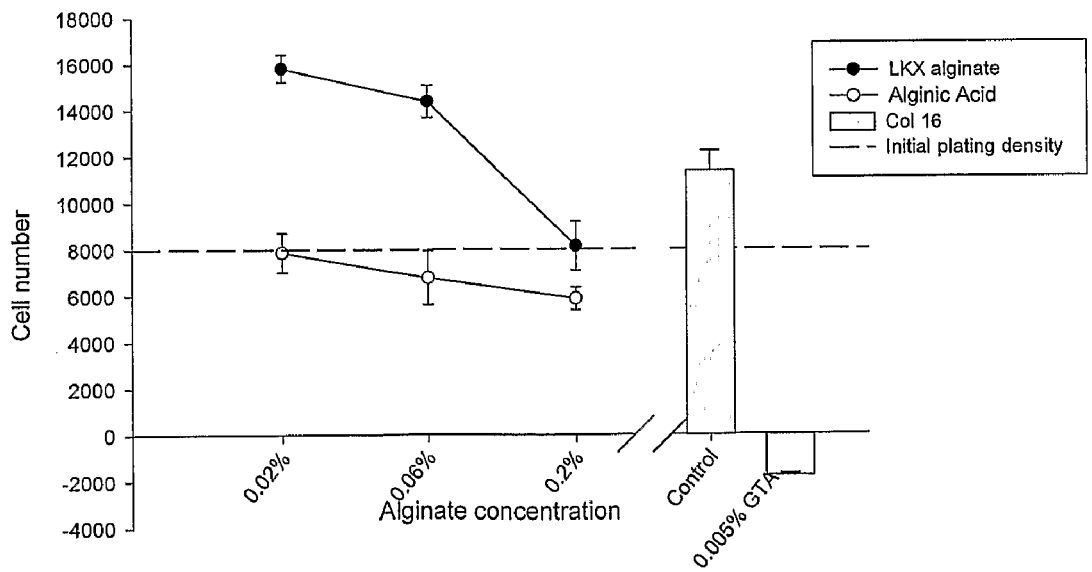

The potential cytotoxic effects of a laboratory grade alginic acid and a pharma grade sodium alginate (both neutralised with sodium hydroxide to pH 7.4) were evaluated over the concentration range 0.02-0.2% and the results are shown in FIG. 35.

Although the laboratory grade alginate caused some cytotoxicity, possibly due to low molecular weight contaminants, this was not seen with the pharma grade alginate. This contributes safety data for the use of alginates as scaffold constituents.

Example 13

Inflammatory Analysis of Scaffold Components (a) Human Neutrophil Activation Assay
(i) Isolation Procedure
Materials Used
Acid Citrate Dextrose (ACD)
Dextran 70
$DiH_2O$ (Sigma purified water)
0.6M NaCl in $DiH_2O$
Dulbecco's PBS with Calcium and Magnesium salts+0.2% glucose (PBS/g)
Trypan Blue (for cell viability count)
Equipment Used
20 ml syringe
Needles for taking blood
Large beaker for storage
15 ml polypropylene tubes
1 ml plastic pipettes
37° C. water bath Dextran 70 and ACD were warmed to 37° C. in a water bath. 2.5 ml ACD was drawn into a 20 ml syringe. 10-15 ml of blood was drawn from a volunteer into the same syringe and inverted several times to mix. The needle was changed and 6-7 ml of Dextran 70 was drawn. Some air was drawn into the top of the syringe and mixed thoroughly by inverting the syringe several times. The syringe was turned upright, taped to the inside of a 37° C. water bath and left for approximately 1.5 hours to allow for erythrocytes to sediment, leaving a leukocyte-rich plasma upper layer.

The syringe was carefully removed from the water bath keeping upright and the top of the needle was bent through about 120°. A 15 ml polypropylene tube was placed under the tip of the needle and approximately half of the plasma was slowly removed (containing the leukocytes). The remainder of the plasma was removed into a second tube leaving the red blood cells in the syringe to be discarded. Each of the 15 ml tubes was topped up with PBS/g and inverted to mix.

The tubes were centrifuged at 1000 rpm for 10 minutes. The supernatant was removed using a 1 ml plastic pipette and the pellet was loosened. If the supernatant appeared cloudy then a check was performed under the microscope for remaining cells and centrifuged again if necessary. When the supernatant was clear it was discarded.

2 ml of $diH_2O$ was added to the cell pellet and vortexed to lyse residual erythrocytes. Exactly 30 seconds after adding the water isotonicity was restored by adding 500 μl 0.6M NaCl and vortexed again.

PBS/g was added to fill the tubes and centrifuged at 1000 rpm for 10 minutes. The supernatant was removed with a plastic pipette, the pellets were resuspended and pooled in one tube in 1-2 ml of PBS/g. A trypan blue cell count was then performed.

(ii) Activation Procedure
Materials Used
PBS/g
Test solutions made up in PBS/g
5 μM PMA in PBS/g (positive control)
PBS
4% PFA/PBS
1% BSA/PBS antibody buffer
0.1% BSA/PBS wash buffer
Primary antibody—Mouse anti-human CD18
Secondary antibody—Rabbit anti-mouse IgG
Equipment Used
5 ml polypropylene tubes
Flow cytometer Cell suspension 0.5-1×10⁶ cells/tube was added to labelled polypropylene tubes for each test condition, including t=0 control, t=1 hour control, an unstained cell control and a secondary antibody only stained cell control.

250 µl of each solution was added to the appropriate tubes. For control tubes, except t=0, 250 µl PBS/g was added. For t=0 control, 250 µl 4% PFA/PBS was added. The tubes were incubated for 1 hour at 37° C.

1 ml PBS/g was added to each tube (except t=0) and centrifuged at 1000 rpm for 4 minutes. The supernatant was tipped off and the cells were resuspended in 250 µl 4% PFA/PBS and left for 15 minutes. Each tube (including t=0) was diluted with 1 ml PBS and spun at 1000 rpm for 4 minutes. The supernatant was tipped off and washed again with PBS. The pellets were resuspended in 0.1% BSA wash buffer and left refrigerated overnight to stain the following day. The unstained control and the secondary antibody only cells were resuspended in 0.1% BSA wash buffer. 100 µl of primary antibody was added to all other cells at a concentration of 10 µg/ml, made up in 1% BSA antibody buffer and incubated at 37° C. for 15 minutes.

1 ml PBS was added to each of the cells stained with antibody and centrifuged at 1000 rpm for 4 minutes. The supernatant was discarded and the cells were resuspended in wash buffer. 1 ml PBS was added to all tubes to be stained with secondary antibody (i.e. all except unstained cells), and centrifuged at 1000 rpm for 4 minutes. The supernatant was discarded and cells were resuspended in 100 µl of 1% BSA antibody buffer containing secondary antibody in the concentration 10 µl in 1 ml.

The cells were incubated and protected from light for between 20 minutes and 1 hour. 1 ml PBS was added to the tubes and spun at 1000 rpm for 4 minutes. The cells were resuspended in 250 µl of 0.1% BSA wash buffer and store protected from light at 4° C. prior to analysis with FACS.

FACS scan analysis was performed using pre-determined instrument settings (Forward scatter, side scatter appropriate to mixed leukocyte samples and Fluorescence detector amplification appropriate for the intensity range of samples), avoiding detector saturation but with adequate amplification over log a 4 decade log scale. The neutrophil population was gated and the mean channel fluorescence of each sample was recorded.

(b) Effect of Glutaraldehyde

Figure 36:
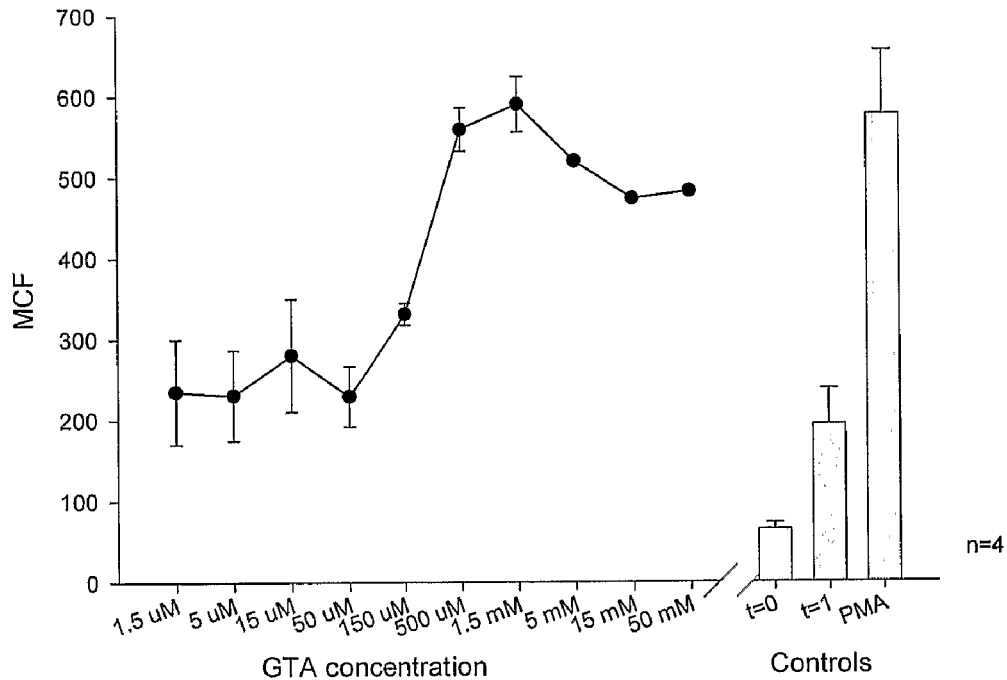
Figure 37:
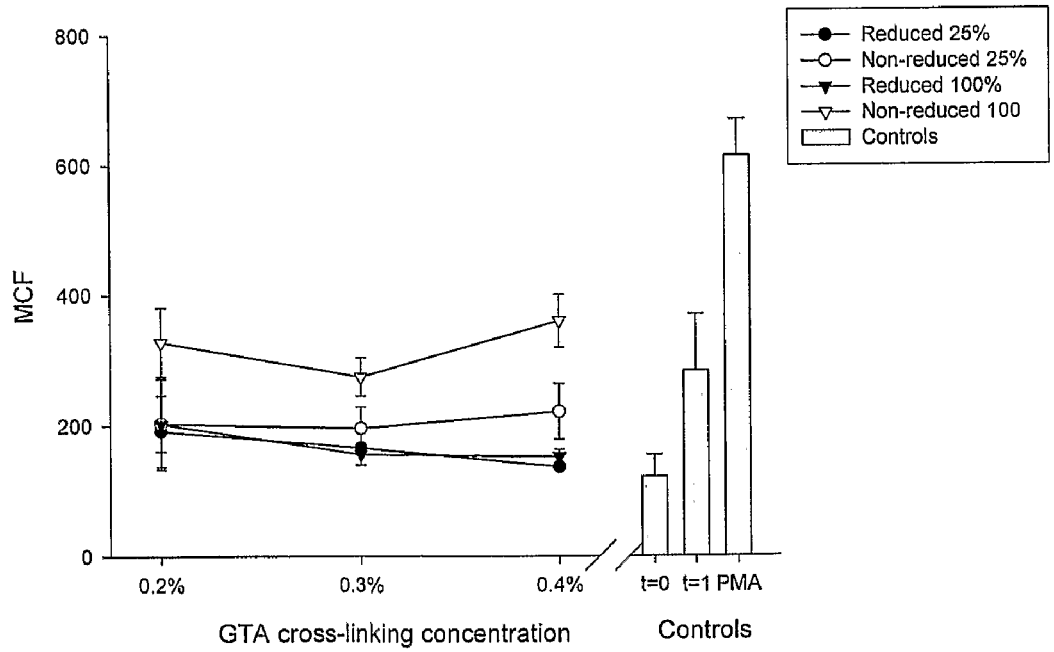
Figure 38:
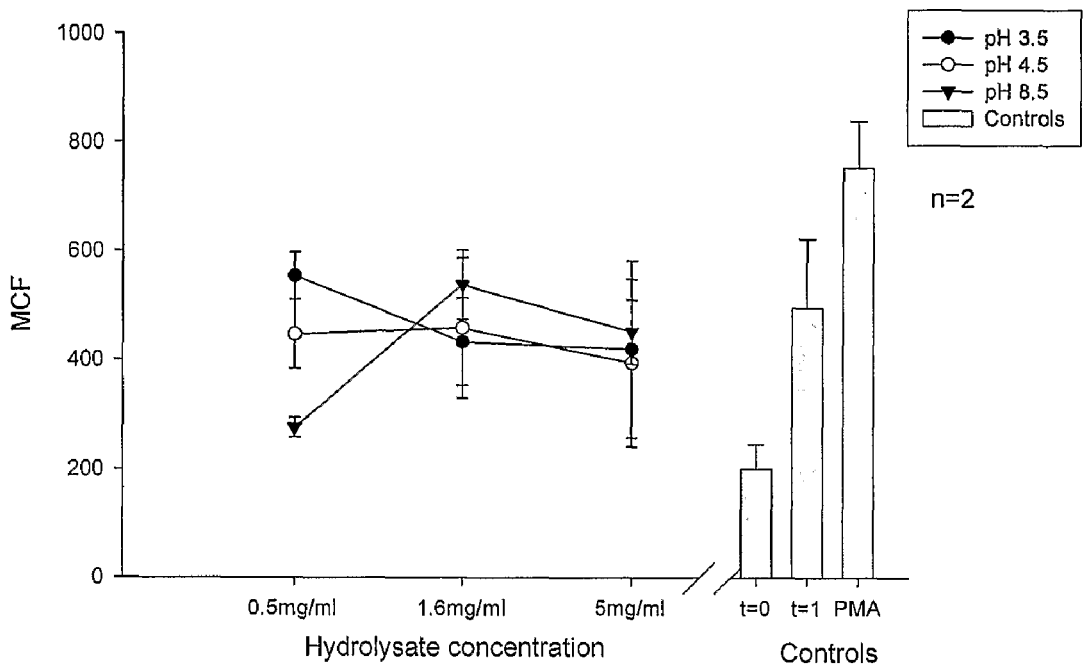
Figure 39:
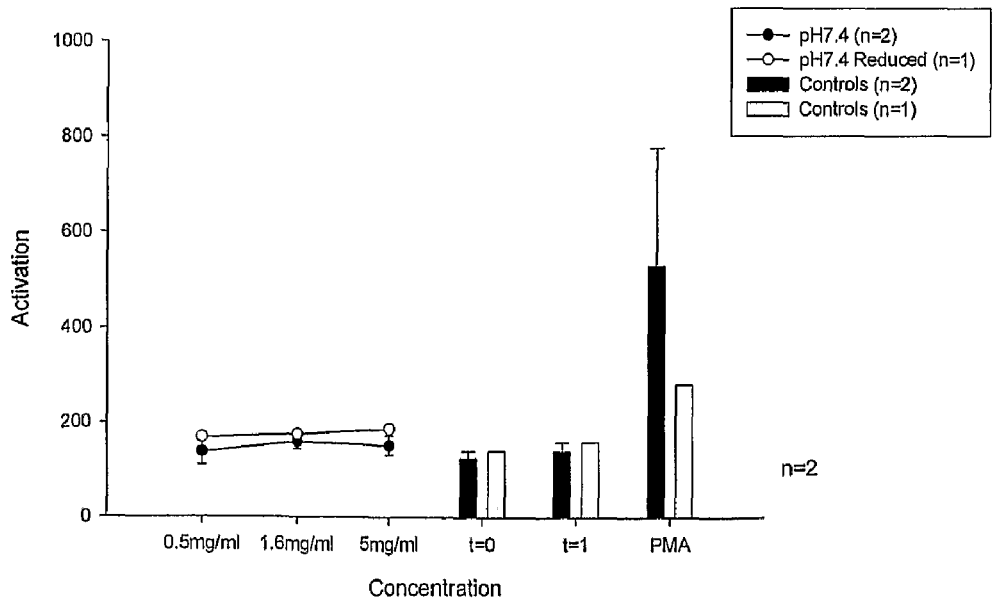

The results for GTA can be seen in FIGS. 36 and 37 wherein GTA has a potent effect on neutrophil CD18 activation, with an $ED_{50}$ around 150-500 µM.

Supernatant PBS from soaking prototype scaffolds (fibrin/alginate/50 mM $CaCl_2$) GTA crosslinked at pH 7.4 for 1 hour, did not cause significant activation of neutrophil CD18. The supernatants from sodium borohydride reduced scaffolds caused lower CD18 than from non-reduced matrices. These data suggest that acute leaching of GTA from scaffolds may be detectable for non-reduced scaffolds, but is below the level of cytotoxicity or neutrophil activation, ie lower than 100 µM, and is further reduced by chemical reduction of the scaffold.

(c) Effect of Schiff Base Residues

Schiff base formation is greater at neutral pH than at pH 3.5, therefore Schiff base residues will be at higher concentration in the corresponding hydrolysates of neutral matrices. The data shown in FIGS. 38 and 39 demonstrates that Schiff base hydrolysates cause little activation, suggesting that degradation products are unlikely to cause neutrophil mediated inflammation. This data which contributes to validating the intrinsic safety of GTA cross-linking.

Comparison of hydrolysates of GTA-crosslinked fibrinogen at pH 7.4, either non-reduced or sodium borohydride reduced samples show no significant neutrophil CD18 activation of either material, demonstrating that sodium borohydride reduction of GTA-crosslinked fibrinogen is unlikely to introduce an inflammatory stimulus into the intrinsic structure of the scaffold.

(d) Effects of Fibrinogen

Figure 40:
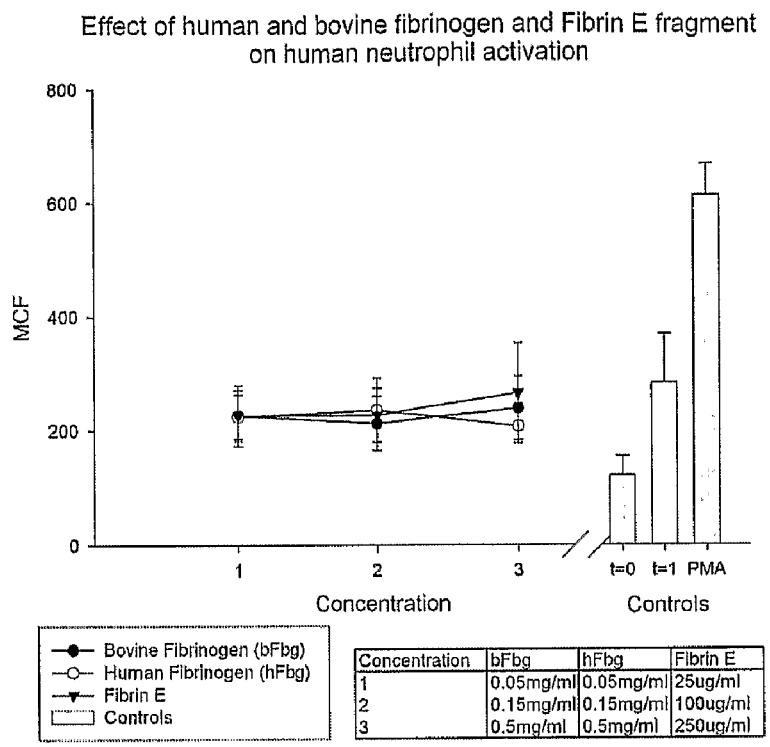

The results for fibrinogen are shown in FIG. 40, wherein neither trypsin nor plasma proteolytic fibrinogen digests as described above cause neutrophil activation. This provides evidence that these proteins in a scaffold are unlikely to cause an inflammatory response.

(e) Effects of Alginates

Figure 41:
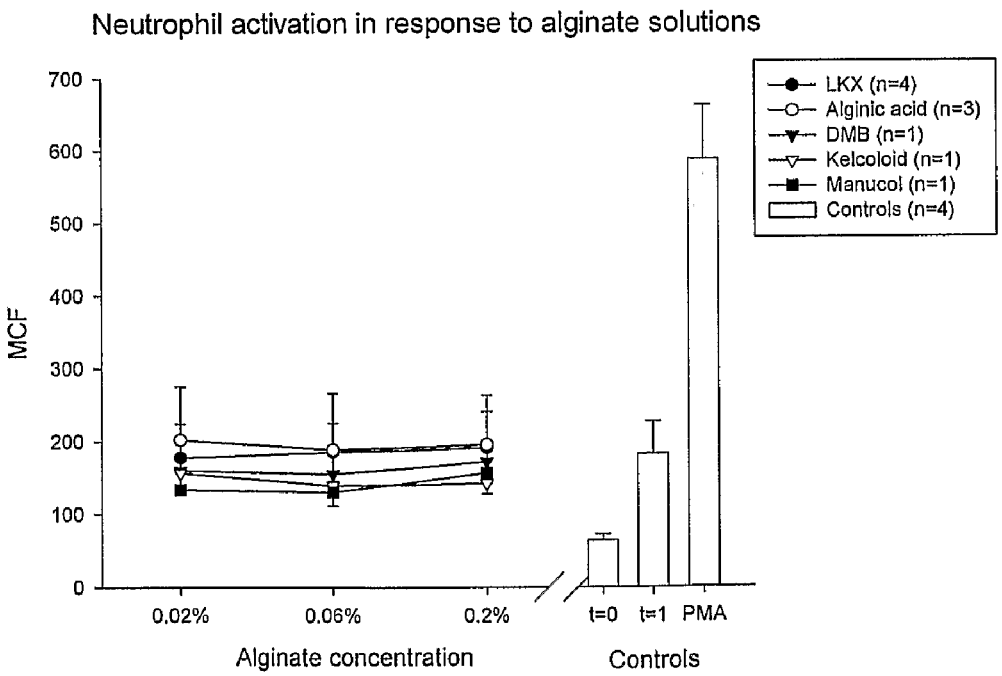

The results for alginates are shown in FIG. 41, wherein neither the laboratory (alginic acid) nor pharma grades of alginate (LKX, Manucol or DMB), nor propylglycol-derivatised alginate (Kelcoloid), caused detectable neutrophil activation. These data give evidence that alginates appear to be safe to use in a scaffold and are unlikely to cause neutrophil-mediated inflammation.

Example 14

In vivo Evaluation of a Fibrin/Alginate/Calcium GTA Cross-Linked, Sodium Borohydride Reduced Foam Scaffold (a) Matrix Manufacture
(i) Materials Used
HEPES/NaCl (25 mM HEPES 150 mM NaCl, pH 7.4);
2% human fibrinogen (fraction 1-type IV-bovine plasma) (F4753, Sigma) in 25 mM HEPES 150 mM NaCl $dH_2O$ (balanced to pH7.4);
2% Fybex™-derived human fibrinogen in 25 mM HEPES 150 mM NaCl pH 7.4;
2% alginic acid (Brown Algae, macrocystitis pyrifera mixed polymer of manuronic acid+glucuronic acid) in 25 mM HEPES 150 mM NaCl $dH_2O$ balanced to pH 7.4;
1M $CaCl_2$ (Sigma) in $dH_2O$;
Human thrombin (EC 3.4.21.5 human plasma, T6884 Sigma), 10 NIHunits/ml in 0.1% BSA/M199 (Gibco);
0.2% glutaraldehyde (25% glutaraldehyde solution Grade II G62517 Sigma) in 80% ethanol (Hayman Ltd, Witham, UK)/20% 100 mM MES pH 7.4 (Used within fume hood due to vent GTA vapour);
Sodium borohydride (Sigma) in $dH_2O$ 1 mg/ml (used within fume hood due to vent hydrogen released gas).
(ii) Equipment Used
Visking tubing (14.3 mm dia, 12-14 kDa, Medicell International, London, UK) and Mediclips;
Magnetic stirrer;
Cold cabinet or cold room (4° C.).
(iii) Dialysis of Fybex™

Fybex™ is a commercially available, surgical haemostatic human fibrin glue system (Bio Product Laboratories, Elstree, UK). It is used as a source of human pathogen-screened fibrinogen and is stabilised for this use by excipients and citrate buffer.

Fybex™ was prepared for matrix manufacture by reconstituting in sterile water as recommended (yielding 5 ml of 60 mg/ml fibrinogen solution per ampoule). This was transferred to 12-14 kDa sterilised visking dialysis tubing sealed with Mediclip clamps dialysis, and dialysed against HEPES/NaCl at 4° C. with stirring by a magnetic stirrer with three changes over 24 hours. Upon completion of dialysis, the purified fibrinogen solution was carefully withdrawn from the tubing and diluted to 20 mg/ml final concentration with 25 mM HEPES 150 mM NaCl solution.

(iv) Matrix Manufacture

To 10 ml fibrinogen solution within a 50 ml centrifuge tube (Greiner Bio One), 1 ml 1M $CaCl_2$ solution (50 mM final concentration) was added, at room temperature under aseptic conditions (flow hood, sterile plasticware). To clot the fibrin over 20 minutes, 150 µl thrombin was added and mixed by brief whisking. Finally, 10 ml alginic acid solution was added (immediately the solution gels in the presence of calcium).

Foam is generated with 30 seconds with the mini-whisk and cast into a 5×5 cm rectangular PTFE 100 ml square weigh boat (Fisherbrand). The foam was incubated for 30 minutes at 37° C. to allow fibrin coagulation in covered trays. (Heraeus HERAcell 150 Incubator, Germany). The foams were transferred to a 4° C. refrigerator for overnight storage.

(v) GTA Crosslinking

Using a sterile scalpel within a sterile flow hood, the corners of the weigh boat were cut open and the matrices freed from within it. The weigh boat-containing matrices were transferred to 100 mm tissue culture petri dishes (Greiner Bio-one), submerged in 15 ml 0.2% glutaraldehyde solution at room temperature, and gently agitated on a flat bed rotating platform at <20 rev/min (Kika Labortechnik KS125 basic).

At 1 hour, the matrix was released from weigh boat and the latter was discarded. Matrix crosslinking was continued for a further 3 hours turning the matrices hourly to ensure adequate glutaraldehyde penetration.

The crosslink solution was then removed, and the matrices were washed with 5 washes of 5 minutes with 15 ml borohydride solution to quench free aldehydes and saturate conjugated diene structures.

Matrices were finally washed with 15 ml $dH_2O$ 3 times.

(vi) Lyophilisation, Storage and Preparation for Surgical Use

The matrices were frozen for at least 4 hours (usually overnight) at −70° C. They were rapidly transferred to the lyophiliser (Christ 1-2 alpha, $4 \times 10^{-4}$ mbar, −60° C. fluid trap) and vacuum dried for 24 hours. Prior to use, the lyophilised matrices were stored in sealed Petri dishes at 4° C.

Immediately, prior to application, in theatre with aseptic technique, the surface of the matrices to be in contact with the wound bed was shaved with 10 blade scalpel, to remove any potential non-porous cortex. The matrices were reconstituted in 5 washes of 15 ml sterile saline (Baxter). This is analogous to the recommended washing procedure described for removal of the 70% glycerol storage solution used for the commercially available scaffold, Integra™.

(b) In Vivo Model (i) Animals, Anaesthesia and Surgery

At the Northwick Park Institute, two out-bred female large white pigs (Bury Farm, Edgware, Middlesex, UK) were employed in this study. The pigs were initially lodged in small groups of two to six animals. In order to avoid inadvertent trauma to the experimental wounds after the first surgical procedure, animals were moved to individual pens in sight of other pigs, each of which opened by a locked gate onto a common walkway. The pigs were fed once daily with approximately 1.5 kg standard pig pellets (J&W Atlee Ltd., Parsonage Mills, Dorking, Surrey, UK). Delousing was performed by a single subcutaneous injection of Ivermectin (Ivomec™, Merial Animal Health, Cambridge, UK) at a dose of 1 ml per 33 kg. Animals were aged 6-7 weeks at the time of the initial surgery. The animals were allowed to settle for 1 week prior to start of the experiment. The mean residency for pigs used in these studies was 34 days. Pigs weighed between 55 and 65 kg at the time of the first surgical procedure and rapidly gained weight, reaching up to 78 kg when euthanised. Animals were sedated with an intramuscular injection of 1 mg·kg$^{-1}$ xylazine (Bayer AnimalHealth, Newbury, UK), and 5 mgkg$^{-1}$ ketamine (Pfizer, Newbury, UK) anaesthesia was induced and maintained using a mixture of 2-5% halothane (IsoFluothane®, Abbott Laboratories, Maidenhead, UK) and 3-5 l min$^{-1}$ of a 50:50 mixture of nitrous oxide and oxygen. For procedures of more than 100 min, animals were intubated with a McGill cuffed 3.5 mm oro-tracheal airway. Peri-operative monitoring was achieved with Doppler oxygen saturation and temperature measurement. Post-operative analgesia was provided by a single sub-cutaneous injection of carprofen (Xenecarp™, Pfizer) at a dose of 4 mg·Kg$^{-1}$. Long acting antibiotic prophylaxis was provided for each procedure by a single pre-operative intramuscular injection of 1.375 g amoxicillin (Amfipen L A, Intervet, Milton Keynes, U K). Euthanasia was carried out after the final procedure by intravenous injection of 25 mg·kg-1 sodium pentobarbitone (Fort Dodge Animal Health, Southampton, UK).

Once anaesthetized, the flanks were shaved and cleaned with aqueous chlorhexidine and betadine solutions and the animal draped. Three circular full-thickness wounds of 4 cm diameter down to muscle fascia were made on the flank of each animal. Haemostasis achieved with bipolar diathermy. Wounds were isolated by percutaneous PTFE chambers (The Bioengineering Department, Northwick Park Institute for Medical Research, Harrow, UK) preventing wound contraction and lateral healing influences. The wounds were reconstructed with either Integra™ synthetic dermal template (Integra Life Sciences, single lot number) or fibrin-based matrix as detailed below. Matrices were immediately adherent but to ensure a stable reconstruction, they were held with a running perimeter 3/0 prolene suture Ethicon, Livingston, UK).

The perimeter of each wound bed was undermined by approximately 1.5 cm to accommodate the rim of the PTFE wound isolation chamber. The chambers were inserted by means of a single vertical extension of the round wound that also allowed access to the initial wound bed to apply the candidate matrices. This vertical wound was closed after insertion and the chamber secured using interrupted 3/0 silk sutures. To reduce infection and prevent drying, the chambers were covered with betadine soaked gauze. The chambers were dressed sequentially with circumferential vellband (Smith and Nephew Healthcare, Hull, UK), Mefix (Molnlycke Healthcare, Dunstable, UK) and Elastoplast Elastic Adhesive Bandage (Beiersdorf-Jobst, Hull, UK). The chambers further protected with a protective jacket fashioned from thermoplastic Spectrum secured with Velcro® straps (Promedics Ltd, Blackburn, Lancashire, UK), and padded with medium density furniture foam (Southern Foam, Crawley, Sussex, UK). The conditions for animal husbandry and anaesthesia were constant for both animals.

Experiments were conducted over a 28 day time course. Biopsies were conducted at day 3, 7, 14 and 28, with the animal euthanised on the final time point. Biopsies were taken by aseptic technique under general anaesthetic. At each time point, 10 mm full thickness punch biopsies through to underlying muscle were harvested (Steifel disposable punch biopsy, High Wycombe, UK) from a single quadrant of the 4 cm PTFE chambers. Photographs of the chambers were taken. The chambers were redressed and further doses of analgesia and antibiotics given. At the final time point, following the punch biopsies from the final quadrant, the PTFE chambers were removed and the remaining reconstructed wound sites were excised en bloc with at least 1 cm of underlying tissue. All biopsies were immediately fixed, for at least 12 hours in 10 ml 4% paraformaldehyde for tissue processing.

4 cm 3 full thickness wounds were created on each flank of a single Yorkshire pig. They were reconstructed within the PTFE chamber with (see FIG. 6.2 for layout);—
- a; Integra T synthetic dermal template
- b; 1% Sigma fibrinogen/1% alginate matrix
- c; 1% Fybex™ fibrinogen/1% alginate matrix The fibrin alginate matrices were approximately 8 mm deep. The Integra T collagen material was approximately 0.3 mm deep, with a silastic backing of similar thickness.

Punch biopsies were harvested at days 3, 8, 14 and 28 from each chamber.

(ii) Histology and Immunohistochemistry

Tissue was paraffin embedded, cut and stained with H&E or immunostained for CD31 (mcab, Dako), von Willebrand factor antigen (mcab, Dako) and α-smooth muscle actin (mcab, Sigma). Control normal human and normal porcine skin was used to validate and optimise antibody reactivity.

(c) Observations

Macroscopically, the prototype scaffolds adhered to the wound bed within minutes of application. The materials were firmly adherent at the first biopsy time and over the of three weeks course they appeared to remain in tact and maintain their original dimensions, with no signs of radial contraction.

Overall, the histological assessment of the wound biopsies throughout the 3 week time course (days 3, 8, 14 & 21) show that:

(i) A leukocyte inflammatory response developed by day 8, which appeared to be confined to a zone which gradually ingressed through the scaffold over the three weeks;

(ii) Most of the depth of test scaffolds were cellularised and degraded by 21 days. The inflammatory response with fibrinogen/alginate scaffolds were greater than for Integra™;

(iii) By day 21, the wounds consisted of a deep layer (up to 10 mm) of granulation/fibroblastic tissue from the fascia of the original wound base. In the case of Integra™, the de novo cellular regeneration extended completely through the scaffold and granulation tissue displaced the silicon membrane by up to 2 mm from the collagenous layer. However, with Integra™, the fibroblastic tissue ingrowth was substantially avascular, and showed a cellular organisation and collagen deposition similar to keloid scar tissue;

(iv) In the cases of prototype Smart matrix, organised & vascularised fibroblastic tissue was deposited behind the inflammatory band of tissue which steadily progressed though the scaffolds. The scaffold substance showed progressive, substantial degradation underneath the inflammatory zone, by day 21; and (v) Little histological difference was seen between scaffolds made from laboratory grade human fibrinogen and Fybex.

(d) Summary of CD31 Immunohistology Results

Figure 42:
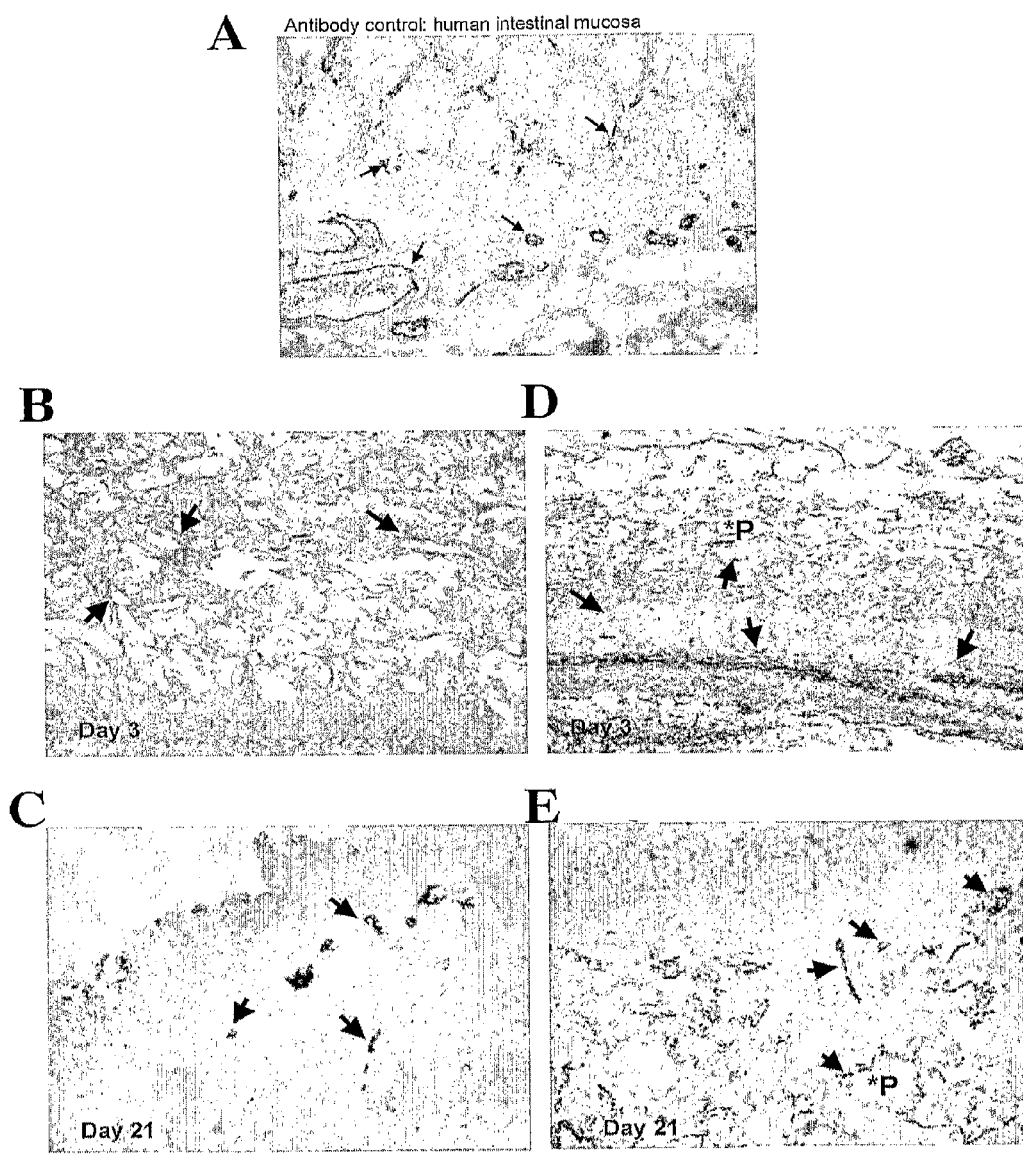

Specific endothelial tissue staining (purple) is evident in normal human mucosa (positive control; FIG. 42A). In day 3 biopsy tissue from the porcine assessment, in Fybex™ treated wound (FIG. 42B), evidence of endothelial cell differentiation or neovascularisation of ingressing granulation tissue is apparent; whereas in Integra™, the CD31 staining in the scaffold appears to be due only to platelets (arrow to *P; FIG. 42D), and endothelial staining is confined to the sub-scaffold granulation zone. The day 21 biopsy tissue from Fybex™ scaffold treated wound (FIG. 42C) shows multiple capillary profiles close to the dorsal surface of the neodermis adjacent to the dorsal remnants of the remodeled scaffold. The day 21 Integra™ (FIG. 42E) shows CD31 staining in extra-fibrobrotic spaces, although these appear to be mainly platelets (arrow to *P), with few plausible capillary profiles (arrows).

VWF immunostaining pattern was similar to CD31. αSM-actin staining showed that granulation tissue was negative for all scaffolds.

This in vivo analysis has clearly demonstrated the following findings:

(i) the materials adhere to the wound bed almost immediately after application;

(ii) the material persists for at least 21 days (but is substantially degraded over this period concomitant with cell ingress and proliferation);

(iii) the regenerated tissue is highly vascular, and organised like provisional dermis (supports rapid cell ingress, visible histologically at day 3);

(iv) wounds do not show overt contraction and the myofibroblast phenotype was not present provides evidence that the test scaffolds may not stimulate scarring.

All these data concord with desirable properties for the scaffold.

Abbreviations
Fbg fibrinogen
GTA glutaraldehyde

The invention claimed is:

1. A process for preparing an extracellular matrix composition which comprises:
   (a) mixing an aqueous solution of fibrinogen with a coagulating agent and a bulking agent and a foaming agent, wherein the mixing step (a) is achieved by foaming;
   (b) incubating the mixture obtained in step (a) with a cross-linking agent selected from: carbodiimide coupling agents including N-(3-dimethylaminopropyl)-N'-ethyl-carbodiimide (EDC); N-hydroxysuccinimide (NHS), azide coupling agents; diisocyanate cross-linking agents including hexamethylene diisocyanate; epoxide cross-linking agents including epi-chlorhydrin, glycidylethers and glycidylamines; and aldehyde cross-linking agents including formaldehyde, glutaraldehyde and glyoxal; and
   (c) washing the cross-linked composition obtained in step (b) to remove the cross-linking agent.

2. The process as defined in claim 1 wherein fibrinogen is present at a purity level of greater than one of 75%, 80%, 85%, 90%, 95%, 97% or 99%.

3. The process as defined in claim 1 wherein fibrinogen is present as truncated forms of fibrinogen, including fibrin A, fibrin B, fibrin C, fibrin D, fibrin X and fibrin Y.

4. The process as defined in claim 3 wherein the truncated form of fibrinogen is fibrin E.

5. The process as defined in claim 1 wherein fibrinogen is present as an aqueous solution buffered to a pH of between 4 and 10 with phosphate buffered saline (PBS) or HEPES buffered saline.

6. The process as defined in claim 1 wherein the coagulating agent is an enzymatic or non-enzymatic coagulating agent.

7. The process as defined in claim 6 wherein coagulating agent is thrombin, including human thrombin.

8. The process as defined in claim 1 wherein the foaming agent is a non-ionic detergent, thermosensitive gelling surfactant, diphosphatydylglycerol type phospholipid or a mixture of an immiscible phase with the aqueous fibrinogen solution phase.

9. The process as defined in claim 1 wherein the bulking agent is an alginate.

10. The process as defined in claim 9 wherein the alginate is sodium alginate.

11. The process as defined in claim 9 wherein the alginate is sodium propylglycoalginate.

12. The process as defined in claim 1 wherein the bulking agent is a glycosaminoglycan (GAG).

13. The process as defined in claim 12 wherein the GAG is selected from chondroitin 6-sulfate, chondroitin 4-sulfate, heparin, heparin sulphate, keratan sulfate, dermatan sulfate, chitin, chitosan, dextran sulphate or hyaluronan.

14. The process as defined in claim 1 wherein the cross linking agent is an aldehyde cross-linking agent including formaldehyde, glutaraldehyde and glyoxal.

15. The process as defined in claim 14 wherein the aldehyde cross-linking agent is glutaraldehyde.

16. The process as defined in claim 14 which additionally comprises addition of a reducing agent or a toxicity reducing agent, including sodium borohydride or lysine.

17. The process as defined in claim 1 wherein the foaming includes mixing with aeration.

18. The process as defined in claim 1 wherein the mixture obtained in step (a) is cast, frozen and optionally lyophilised prior to the incubation step (b).

19. The process as defined in claim 1 which additionally comprises addition of a divalent or multivalent metal ion including calcium.

20. The process as defined in claim 19 wherein calcium is in the form of calcium chloride.

21. A method of in vitro, ex vivo or in vivo wound healing or tissue regeneration, comprising applying the extracellular matrix composition produced by the process defined in claim 1 to a wound.

* * * * *